(12) United States Patent
Schief et al.

(10) Patent No.: US 9,718,862 B2
(45) Date of Patent: Aug. 1, 2017

(54) POLYPEPTIDES AND THEIR USE IN TREATING AND LIMITING RESPIRATORY SYNCYTIAL VIRUS INFECTION

(75) Inventors: William R. Schief, Encinitas, CA (US); Bruno E. Correia, San Diego, CA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 288 days.

(21) Appl. No.: 13/878,122

(22) PCT Filed: Oct. 6, 2011

(86) PCT No.: PCT/US2011/055113
§ 371 (c)(1),
(2), (4) Date: Jul. 11, 2013

(87) PCT Pub. No.: WO2012/048115
PCT Pub. Date: Apr. 12, 2012

(65) Prior Publication Data
US 2013/0280262 A1 Oct. 24, 2013

Related U.S. Application Data

(60) Provisional application No. 61/390,591, filed on Oct. 6, 2010.

(51) Int. Cl.
*C07K 14/00* (2006.01)
*A61K 39/12* (2006.01)
*C07K 14/005* (2006.01)
*G06F 19/16* (2011.01)
*A61K 39/00* (2006.01)

(52) U.S. Cl.
CPC .......... *C07K 14/001* (2013.01); *A61K 39/12* (2013.01); *C07K 14/005* (2013.01); *G06F 19/16* (2013.01); *A61K 39/00* (2013.01); *A61K 2039/552* (2013.01); *A61K 2039/55566* (2013.01); *A61K 2039/6075* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| | | |
|---|---|---|
| 5,334,394 A | 8/1994 | Kossovsky et al. |
| 5,770,380 A | 6/1998 | Hamilton et al. |
| 7,097,841 B2 | 8/2006 | Carter et al. |
| 7,229,618 B2 | 6/2007 | Johnson et al. |
| 7,229,624 B2 | 6/2007 | Renner et al. |
| 7,700,720 B2 | 4/2010 | Tous et al. |
| 2011/0236408 A1 | 9/2011 | Morrison |
| 2012/0315270 A1 | 12/2012 | McLellan et al. |
| 2015/0050306 A1 | 2/2015 | Schief et al. |

FOREIGN PATENT DOCUMENTS

| | | |
|---|---|---|
| AU | 2011311946 | 10/2014 |
| AU | 2011311946 B8 | 1/2015 |
| CN | 1668335 A | 9/2005 |
| CN | 103282378 A | 9/2013 |
| CN | 201180058569.8 | 3/2015 |
| EP | 2834263 | 2/2015 |
| EP | 2625194 | 8/2015 |
| EP | 2625194 B1 | 8/2015 |
| JP | 2014-502143 | 1/2014 |
| JP | 2014-502143 A | 1/2014 |
| WO | 2008/025015 | 2/2008 |
| WO | 2009/079796 | 7/2009 |
| WO | 2009/100376 | 8/2009 |
| WO | 2011/050168 | 4/2011 |
| WO | 2012048115 A2 | 4/2012 |
| WO | 2013/152274 | 10/2013 |
| WO | 2013152274 A1 | 10/2013 |

OTHER PUBLICATIONS

McLellan et al., J. Mol. Biol. (2011) 409, 853-866.*
Weisshaar et al. DNA and Cell Biology 2015, vol. 34, pp. 505-510.*
Zhu et al. (2011) "Analysis of respiratory syncytial virus preclinical and clinical variants resistant to neutralization by monoclonal antibodies palivizumab and/or motabvizumab," Journal Infect Dis, 203(5):674-82.
Wilson et al. (1992) "Hepatocyte-directed gene transfer in vivo leads to transient improvement of hypercholesterolemia in low density lipoprotein receptor-deficient rabbits," J. Biol. Chem. 267:963-967.
Wu, et al., (2010), "Rational Design of Envelope Identifies Broadly Neutralizing Human Monoclonal Antibodies to HIV-1," Science 329:856.
Rohl et al., (2004), "Protein structure prediction using Rosetta," Methods in Enzymology 383: 66-93.
McLellan et al., "Design and Characterization of Epitope Scaffold Immunogens that present the Motavizumab Epitope from Respiratory Syncytial Virus," J. Mol. Biol. (2011) 409, 853-866.
Wu, et al., (2007) "Development of Motavizumab an ultra-potent antibody for the prevention of respiratory Syncytial virus infection in the upper and lower respiratory tract," Journal of Molecular Biology, 368(3): 652-665.
Zlotnick et al., (1996) "Dimorphism of hepatitis B virus capsids is strongly influences by the C-terminus of the capsid protein," Biochemistry, 35(23): 7412-21.
Wynne et al., (1999), "The crystal structure of the human hepatitis B virus capsid," Mol Cell, 3(6):771-80.
Bradley, et al., (2006), "Improved beta-proteins structure prediction by multilevel optimization of nonlocal strand pairing and local backbone conformation," Proteins, 65(4): 922-9.
Simons, et al., (1997), "Assembly of protein tertiary structures from fragments with similar local sequences using simulated annealing and Bayesian scoring functions," J Mol Biol., 268(1); 209-25.
International Search Report for PCT/US2011/05511, mailed Apr. 27, 2012.

(Continued)

*Primary Examiner* — Shanon A Foley
*Assistant Examiner* — Myron Hill
(74) *Attorney, Agent, or Firm* — McDonnell Boehnen Hulbert & Berghoff LLP

(57) ABSTRACT

The present invention provides polypeptides and compositions thereof for treating or limiting respiratory syncytial virus infection, and computational methods for designing such polypeptides.

19 Claims, 8 Drawing Sheets

(56) References Cited

OTHER PUBLICATIONS

McLellan, et al., "Structural basis of Respiratory syncytial virus neutralization by motavizumab," Nature Struct. Mol. Bio. (Feb. 2010) 17(2): 248-250.
McLellan, et al., "Design and Characterization of Epitope-Scaffold Immunogens that present the Motavizumab epitope from respiratory syncytial virus," Journal of Molecular Biology, (Apr. 2011) 409: 853-866.
McLellan et al., (2010) "structure of a major antigenic site on the respiratory syncytial virus fusion glycoprotein in complex with neutralizing antibody 101F," Journal of Virology, 84(23): 12236-12244.
McLellan et al., (2011) "Structure of Respiratory Syncytial virus fusion glycoprotein in the postfusion conformation reveals preservation of neutralizing epitopes," Journal of Virology, 85(15): 7788-7796.
R. Das and D. Baker (Jul. 2008) "Macromolecular modeling with Rosetta," Annual Review of Biochemistry, 77:363-382.
J. Arbiza et al. (Sep. 1992) "Characterization of two antigenic sites recognized by neutralizing monoclonal antibodies directed against the fusion glycoprotein of human respiratory syncytial virus," Journal of General Virology, 73(Pt 9):2225-2234.
BE Correia et al. (Jan. 2011) "Computational protein design using flexible backbone remodeling and resurfacing: case studies in structure-based antigen design," Journal of Molecular Biology, 405(1):284-297.
EP 11773937.5, EP Office Action dated Mar. 28, 2014.
EP 11773937.5, EP Office Action dated Nov. 17, 2014.
EP 11773937.5, EPO Intention to Grant dated Mar. 4, 2015.
AU 2011311946, AU first Examination Report dated Aug. 6, 2014.
CN 201180058569.8, CN Office Action dated Apr. 30, 2014.
JP 2014-502143, JP Office Action dated Sep. 15, 2015.
BE Correia et al. (Sep. 2010) "Computational design of epitope-scaffolds allows induction of antibodies specific for a poorly immunogenic HIV vaccine epitope," Structure, 18(9):1116-1126.
G. Ofek et al. (Sep. 2010) "Elicitation of structure-specific antibodies by epitope scaffolds," Proceedings of the National Academy of Sciences USA, 107(42):17880-17887.
DR Burton (Oct. 2010) "Scaffolding to build a rational vaccine design strategy," Proceedings of the National Academy of Sciences USA, 107(42):17859-17860.
X. Zhao et al. (Dec. 2004) "Variable resistance to palivizumab in cotton rats by respiratory syncytial virus mutants," Journal of Infectious Diseases, 190(11):1941-1946.
JA Lopez et al. (Dec. 1993) "Conformational constraints of conserved neutralizing epitopes from a major antigenic area of human respiratory syncytial virus fusion glycoprotein," Journal of General Virology, 74(12):2567-2577.
BE Correia et al. (Mar. 2014) "Proof of principle for epitope-focused vaccine design," Nature, 507(7491):201-206.
International Search Report and Written Opinion for PCT/US2013/035408 dated Aug. 19, 2013.
JS McLellan et al. (Aug. 2011) "Structure of Respiratory Syncytial Virus Fusion Glycoprotein in the Postfusion Conformation Reveals Preservation of Neutralizing Epitopes," Journal of Virology, 85(15):7788-7796.
JS McLellan et al. (Dec. 2010) "Structure of a Major Antigenic Site on the Respiratory Syncytial Virus Fusion Glycoprotein in Complex with Neutralizing Antibody 101F," Journal of Virology, 84(23):12236-12244.
International Search Report for PCT/US2013/035488 dated Aug. 19, 2013.
JS McLellan et al. (2011) "Design and Characterization of Epitope-Scaffold Immunogens That Present the Motavizumab Epitope from Respiratory Syncytial Virus," Journal of Molecular Biology, 409: 853-866.
Adams et al. (Nov. 2002) "PHENIX: building new software for automated crystallographic structure determination," Acta Crystallographica Section D: Biological Crystallography, 58(Pt 11):1948-1954.

Alexander et al. (Dec. 1994) "Development of high potency universal DR-restricted helper epitopes by modification of high affinity DR-blocking peptides," Immunity, 1(9):751-761.
Arbiza et al. (Sep. 1992) "Characterization of two antigenic sites recognized by neutralizing monoclonal antibodies directed against the fusion glycoprotein of human respiratory syncytial virus," Journal of General Virology, 73(Pt 9)2225-2234.
Aricescu et al. (Oct. 2006) "A time- and cost-efficient system for high-level protein production in mammalian cells," Acta Crystallographica Section D: Biological Crystallography, 62(Pt 10):1243-1250.
Barourch et al. (Jul. 2005) "A human T-cell leukemia virus type 1 regulatory element enhances the immunogenicity of human immunodeficiency virus type 1 DNA vaccines in mice and nonhuman primates," Journal of Virology, 79(14):8828-8834.
Beeler and K. van Wyke Coelingh (Jul. 1989) "Neutralization epitopes of the F glycoprotein of respiratory syncytial virus: effect of mutation upon fusion function," Journal of Virology, 63(7):2941-2950.
Bryson et al. (Jul. 2005) "Protein structure prediction servers at University College London," Nucleic Acids Research, 33(Web Server issue):W36-W38.
Burton (Oct. 2010) "Scaffolding to build a rational vaccine design strategy," Proceedings of the National Academy of Sciences USA, 107(42):17859-17860.
Chargelegue et al. (Mar. 1998) "A Peptide Mimic of a Protective Epitope of Respiratory Syncytial Virus Selected from a Combinatorial Library Induces Virus-Neutralizing Antibodies and Reduces Viral Load In Vivo," Journal of Virology, 72(3):2040-2046.
CN 1st Office Action dated Apr. 30, 2014.
Correia et al. (Jan. 2011) "Computational protein design using flexible backbone remodeling and resurfacing: case studies in structure-based antigen design," Journal of Molecular Biology, 405(1):284-297.
Correia et al. (Sep. 2010) "Computational Design of Epitope-Scaffolds Allows Induction of Antibodies Specific for a Poorly Immunogenic HIV Vaccine Epitope," Structure, 18(9)1116-1126.
Correia et al. (Mar. 2014) "Proof of principle for epitope-focused vaccine design," Nature, 507(7491):201-206.
Das and D. Baker (Jul. 2008) "Macromolecular Modeling with Rosetta," Annual Review of Biochemistry, 77:363-382.
Emsley and K. Cowtan (Dec. 2004) "Coot: model-building tools for molecular graphics," Acta Crystallographica Section D: Biological Crystallography, 60(Pt 12 Pt 1):2126-2132.
EP Intention to Grant dated Mar. 4, 2015 for EP 2625194.
EP Office Action dated Mar. 28, 2014 for EP 2625194.
EP Office Action dated Nov. 17, 2014 for EP 2625194.
First Examination Report dated Aug. 6, 2014 for AU 2011311946.
GenBank: AAS93649.1. Fusion protein [Human respiratory syncytial virus]. (May 2005) available online at: http://www.ncbi.nlm.nih.gov/protein/AAS93649.
Groothuis et al. (Apr. 1995) "Respiratory syncytial virus (RSV) infection in preterm infants and the protective effects of RSV immune globulin (RSVIG). Respiratory Syncytial Virus Immune Globulin Study Group," Pediatrics, 95(4):463-467.
Hallak et al. (Jun. 2000) "Iduronic acid-containing glycosaminoglycans on target cells are required for efficient respiratory syncytial virus infection," Virology, 271(2):264-275.
International Search Report and Written Opinion dated Sep. 21, 2011 for PCT/US2010/053558 filed Oct. 21, 2010, 22 pages.
International Search Report and Written Opinion dated Apr. 27, 2012 for PCT/US2011/055113 filed Oct. 6, 2011.
International Search Report and Written Opinion dated Aug. 19, 2013 for PCT/US2013/035408 filed Apr. 5, 2013.
Johnson et al. (Nov. 1997) "Development of a humanized monoclonal antibody (MEDI-493) with potent in vitro and in vivo activity against respiratory syncytial virus," Journal of Infectious Diseases, 176(5):1215-1224.
JPO 1st Office Action dated Sep. 15, 2015.
Krissinel and K. Henrick (Sep. 2007) "Inference of macromolecular assemblies from crystalline state," Journal of Molecular Biology, 372(3):774-797.

(56) References Cited

OTHER PUBLICATIONS

Larkin et al. (Nov. 2007) "Clustal W and Clustal X version 2.0," Bioinformatics, 23(21):2947-2948.
Lawrence and PM Colman (Dec. 1993) "Shape complementarity at protein/protein interfaces," Journal of Molecular Biology, 234(4):946-950.
Liu et al. (Sep. 2008) "Molecular architecture of native HIV-1 gp120 trimers," Nature, 455(7209):109-113.
Lok et al. (Mar. 2008) "Binding of a neutralizing antibody to dengue virus alters the arrangement of surface glycoproteins," Nature Structural & Molecular Biology, 15(3):312-317.
Lopez et al. (1998) J Virol, 72:6922-6928.
López et al. (Dec. 1993) "Conformational constraints of conserved neutralizing epitopes from a major antigenic area of human respiratory syncytial virus fusion glycoprotein," Journal of General Virology, 74(Pt 12):2567-2577.
McCoy et al. (Aug. 2007) "Phaser crystallographic software," Journal of Applied Crystallography, 40(Pt 4):658-674.
McLellan et al. (Feb. 2010) "Structural basis of respiratory syncytial virus neutralization by motavizumab," Nature Structural & Molecular Biology, 17(2):248-250.
Mejias et al. (Oct. 2007) "Motavizumab, a neutralizing anti-Respiratory Syncytial Virus (Rsv) monoclonal antibody significantly modifies the local and systemic cytokine responses induced by Rsv in the mouse model," Virology Journal, 4:109.
Ofek et al. (Oct. 2010) "Elicitation of structure-specific antibodies by epitope scaffolds," Proceedings of the National Academy of Sciences USA, 107(42):17880-17887.
Otwinowski and W. Minor (1997; retrieved May 2016) "[20] Processing of X-ray diffraction data collected in oscillation mode," Methods in Enzymology, 276:307-326.
Pastor et al. (Dec. 2007) "Resdesign of protein domains using one-bead-one-compound combinatorial chemistry," Journal of the American Chemical Society, 129(48):14922-14932.
Sia et al. (Aug. 2003) "Protein grafting of an HIV-1 inhibiting epitope," Proceedings of the National Academy of Sciences USA, 100(17):9756-9761.
Smith et al. (May 2002) "Modelling the structure of the fusion protein from human respiratory syncytial virus," Protein Engineering, 15(5):365-371.
Tao et al. (Jun. 1997) "Structure of bacteriophage T4 fibritin: a segmented coiled coil and the role of the C-terminal domain," Structure, 5(6):789-798.
The IMpact-RSV Study Group (Sep. 1998) "Palivizumab, a humanized respiratory syncytial virus monoclonal antibody, reduces hospitalization from respiratory syncytial virus infection in high-risk infants," Pediatrics, 102(3):531-537.
Thompson et al. (Jan. 2003) "Mortality associated with influenza and respiratory syncytial virus in the United States," Journal of the American Medical Association (JAMA), 289(2):179-186.
Wu et al. (Jul. 2005) "Ultra-potent antibodies against respiratory syncytial virus: effects of binding kinetics and binding valence on viral neutralization," Journal of Molecular Biology, 350(1):126-144.
Wu et al. (Oct. 2007) "Characterization of the epitope for anti-human respiratory syncytial virus F protein monoclonal antibody 101F using synthetic peptides and genetic approaches," Journal of General Virology, 88(Pt 10):2719-2723.
Yin et al. (Jan. 2006) "Structure of the parainfluenza virus 5 F protein in its metastable, prefusion conformation," Nature, 439(7072):38-44.
Zhao et al. (Dec. 2004) "Variable resistance to palivizumab in cotton rats by respiratory syncytial virus mutants," Journal of Infectious Diseases, 190(11):1941-1946.
McClellan, et al., "Structure of RSV Fusion Glycoprotein Trimer Bound to a Prefusion-Specific Neutralizing Antibody," Science, 340: 1113-1117, May 2013.

* cited by examiner

```
GSMSDRRKDLEERLDKILEAAKNKEDKFKAAMRKKRGQREERMKDWAKIARDEFEQFRKAV  60  PFL_003
GSMSDARKDLEERLDKILEAAKNKMDKFKAAMRKKRGQREERKKDWAKIVRDEFBQFRKAV  60  PFL_004
GSLSDIRKDAERRFDKLVEAVKNKLDKMKAALRKEGQQEERMKDLMKFMRKEVEQLRKKAM  60  PFL_007
GSRSDMRKDAERRFDKFVEAAKNKFDKFKAALRKGDIKEEERRKDMKKLARKEAEQARRAV  60  PFL_001
GSLSDVRKDVEKRIDKALEAFKNKMDKEKAAFRKDPPSEEERRKDKKKEFREEREQVRKAI  60  PFL_002
GSFSDIRKDAEDRADKAFEAAKNKFDKIKAAIRKDWPSEERAKDLMKKARYEMEQARRAI  60  PFL_006
GSLSDLMKDLEKRFDKFMEAIKNKWDKVKAAFRKQEKCEERAKDMFKIFREELEQLRKKAI  60  PFL_008
GSMSDIRKDLEERFDKLVEALKNKVDKMKAAFRKDQFHEERMKDWFKDLRKEVEQMRRAV  60  PFL_005
GSISDIRKDAEVRMDKAVEAFKNKLDKFKAAVRKVFPTEERIKDMLKIVRGEABQARVAV  60  T93
*** ** * **   *** ** ****       *        *      ** ** * *;

RNFLSEALSKIN------DYPITNDKKLITSNDAKKFDAEVAKKLEAFKADAEEAATQ---  112  PFL_003
RNFLSEALSKIN------DYPITNDKKLITSNDTKKFAAEVEKKLEAFKADVEEAATQ---  112  PFL_004
RNFLSEALSKIN------DMPITNDKKLISNDLKKYDAIAEKKLEAMKADVERMATQGSW  115  PFL_007
RNRLSELLSKIN------DMPITNDQKKLMSNDVLKFAAEAEKKIEALALAADAEDKFTQGSW  115  PFL_001
RNVLSEALSKIN------DLPITNDKKKLVSNDVIKKVAEMKKKVELEVADVERKKVTQGSW  115  PFL_002
RNIESEALSKIN------DLPITNDQKKLASNDIIKEMARLFKKLEALMADIEILVTQ---  112  PFL_006
RNALSEALSKIN------DLPITNDKKLASNKAKKRAARVMKKVEAFIADVEAWKTQ---  112  PFL_008
RNYASEALSKIN------DLPITNDKKLASNDVLKLVAEVNKKLEAILADVEANFTQ---  112  PFL_005
RNVGRDAMDKAAALGKDKEINWFDISQSLMDVQKLTDAAIKKIEAALADMEAWLTQ---  116  T93
**                *  *** **       *            **  **;     *
```

Figure 3

US 9,718,862 B2

POLYPEPTIDES AND THEIR USE IN TREATING AND LIMITING RESPIRATORY SYNCYTIAL VIRUS INFECTION

CROSS REFERENCE

This application is a U.S. national phase of International Application No. PCT/US2011/055113 filed Oct. 6, 2011, which claims priority to U.S. Provisional Application Ser. No. 61/390,591 filed Oct. 6, 2010, the disclosures of which are incorporated herein by reference in their entirety.

BACKGROUND

Respiratory Syncytial Virus (RSV) is the leading cause of viral death in infants worldwide and also causes disease in the elderly and immune-compromised. The current method for preventing RSV infection is passive immunization with Palivizumab (Pali), an FDA-licensed humanized monoclonal antibody that binds the F protein on the RSV surface. Though effective at preventing RSV infection, Pali treatment is not economically or logistically feasible on a global scale.

SUMMARY OF THE INVENTION

In a first aspect, the present invention provides isolated polypeptides comprising an amino acid sequence according to any of SEQ ID NOS:1-9, which can be used, for example, in the methods of the invention.

In another aspect, the present invention provides virus-like particles comprising the polypeptide of the invention.

In further aspects, the present invention provides isolated nucleic acids encoding the polypeptides of the invention; recombinant expression vectors comprising the isolated nucleic acids of the invention operatively linked to a promoter; and recombinant host cells comprising the recombinant expression vectors of the invention.

In a still further aspect, the present invention provides pharmaceutical compositions, comprising the polypeptide and/or virus-like particles of the invention, and a pharmaceutically acceptable carrier.

In another aspect, the present invention provides methods for treating a RSV infection, comprising administering to a subject infected with RSV an amount effective to treat the infection of the polypeptides, virus-like particles, or pharmaceutical compositions of the invention In a further aspect, the present invention provides methods for limiting development of an RSV infection, comprising administering to a subject at risk of RSV infection an amount effective to limit development of an RSV infection of the polypeptides, virus-like particles, or pharmaceutical compositions of the invention.

In a still further aspect, the present invention provides methods for generating an immune response in a subject, comprising administering to the subject an amount effective to generate an immune response of the polypeptides, virus-like particles, or pharmaceutical compositions of the invention.

In another aspect, the present invention provides pharmaceutical composition, comprising
 (a) isolated nucleic acids, recombinant expression vectors, and/or recombinant host cells of the invention; and
 (b) a pharmaceutically acceptable carrier.

In a further aspect, the present invention provides methods for monitoring an RSV-induced disease in a subject and/or monitoring response of the subject to immunization by an RSV vaccine, comprising contacting the polypeptides, the VLPs, or the pharmaceutical compositions of the invention with a bodily fluid from the subject and detecting RSV-binding antibodies in the bodily fluid of the subject.

In a still further aspect, the present invention provides methods for detecting RSV binding antibodies, comprising
 (a) contacting the polypeptides, the VLPs, or the compositions of the invention with a composition comprising a candidate RSV binding antibody under conditions suitable for binding of RSV antibodies to the polypeptide, VLP, or composition; and
 (b) detecting RSV antibody complexes with the polypeptide, VLP, or composition.

In another aspect, the present invention provides methods for producing RSV antibodies, comprising
 (a) administering to a subject an amount effective to generate an antibody response of the polypeptides, the VLPs, and/or the compositions of the invention; and
 (b) isolating antibodies produced by the subject.

In another aspect, the present invention provides computational methods for designing a polypeptide scaffold, comprising
 (a) defining a polypeptide structural motif to be used as a folding nucleus;
 (b) defining (i) a target three dimensional topology for a polypeptide scaffold compatible with the polypeptide structural motif, and (b) a region of the target three dimensional topology to be replaced by the polypeptide structural motif;
 (c) growing an extended polypeptide chain from termini of atomic coordinates of the polypeptide structural motif;
 (d) folding the extended polypeptide chain while maintaining backbone dihedral angles of the polypeptide structural motif fixed; and
 (e) identifying folded polypeptide chains that meet a user-defined threshold of polypeptide backbone root mean square deviation (rmsd) relative to the target three-dimensional topology as polypeptide scaffolds of interest.

In a further aspect, the present invention provides non-transitory machine readable storage medium, comprising a set of instructions for causing a computing device to carry out the computational methods of the invention.

BRIEF DESCRIPTION OF THE DRAWINGS

FIG. 3 is a sequence alignment of the different scaffolds and the sequence of the protein used as target topology (T93). The similarities in many of the positions were imposed by the surface that in the scaffolds was intentionally maintained the same as the target topology (from top to bottom SEQ ID NOs: 10, 6, 9, 4, 5, 8, 12, 7, and 11).

DETAILED DESCRIPTION OF THE INVENTION

Figure 1:
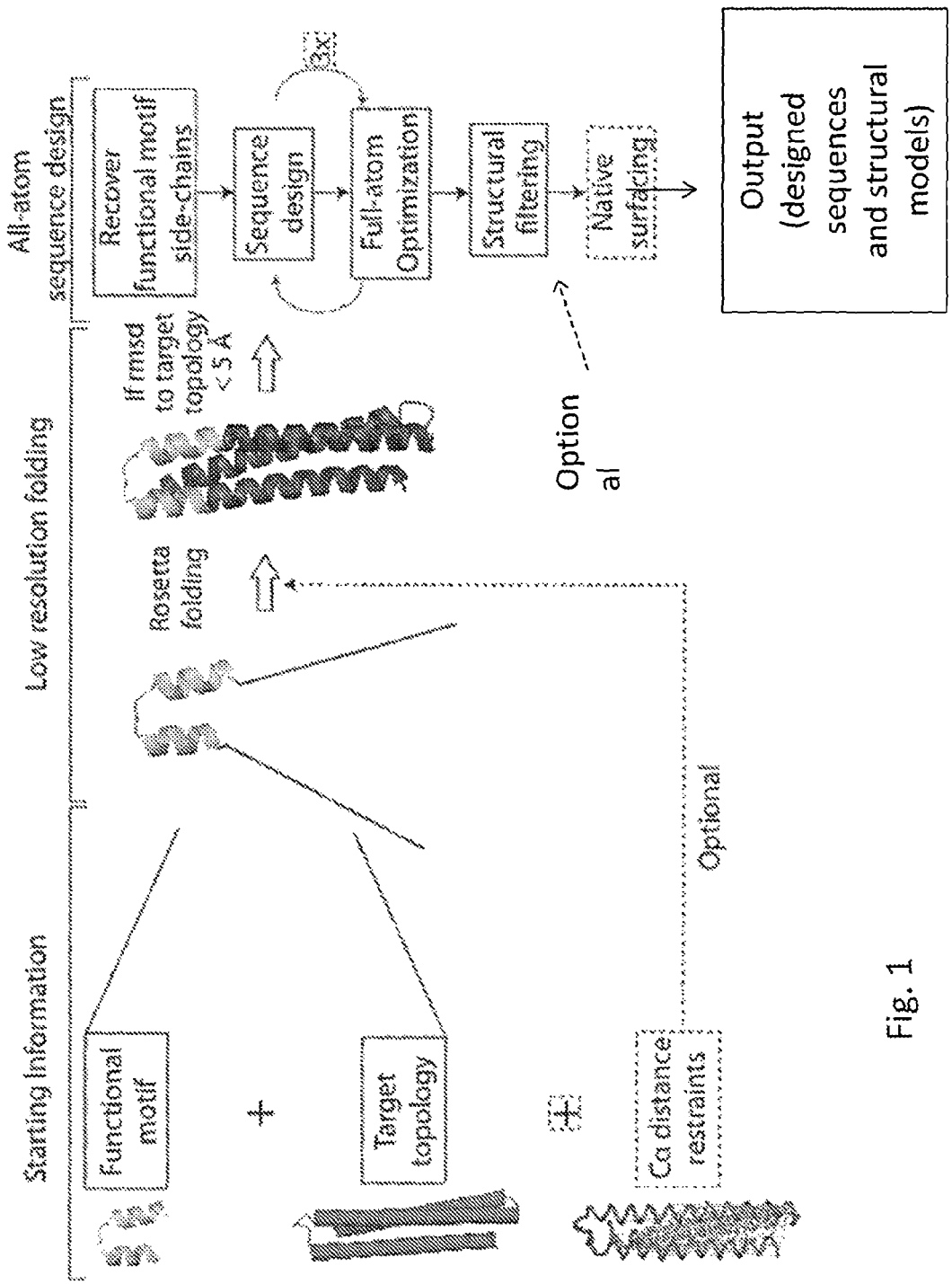
FIG. 1 is an overview of the computational procedure Fold From Loops. The procedure takes a functional site (such as the helical hairpin shown) that will be used as the folding nucleus and remain in fixed backbone conformation throughout the procedure. A target topology is supplied and distance constraints are (optionally) derived from the target topology structure to guide the folding trajectory. The polypeptide chain is extended from the folding nucleus and the chain is then folded. If the models produced are more than a cutoff root mean square deviation (rmsd) (e.g. 5 Å) away from the target topology, they are discarded. Otherwise, they enter cycles of design and full-atom optimization. The figure depicts 3 cycles of iterative design and optimization as a reasonable choice, but the number of cycles is to be chosen at the discretion of the user.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides isolated polypeptides, comprising or consisting of an amino acid sequence according to the following:

```
                                                           (SEQ ID NO: 1)
(-/G)(-/S)(M/L/R/F)SD(R/A/I/M/V/L)(R/M)KD(L/A/V)E(E/R/K/D)R(L/F/I/A)DK(L/F/A)

(L/V/F/M)EA(AN/F/I/L)KNK(E/M/L/F/W/V)DK(F/M/E/I/V)KAA(M/L/F/I)RK(R/E/G/D/Q)

(G/D/P/W/E/Q)(Q/I/P/K/F)(R/Q/K/S/G/H)EER(M/K/R/A)KD(W/L/M/K)(A/M/K/F)K (I/F/L/E/K/D)(A/V/M/F/L)R(D/K/E/Y)E(F/V/A/R/M/L)EQ(F/L/A/V/M)R(K/R)A(V/M/I)

RN(F/R/V/I/A/Y)(L/E/A)(S)(E)(A/L)(L)(S)K(I)(N)D(Y/M/L)(P)I(T)(N)(D)(D/Q/K)

(K)(K)(L)(T/I/M/V/A)(S)(N)(D/K)(A/T/L/V/I)(K/L/I)K(F/Y/K/E/R/L)(D/A/V/M)(A)

(E/I/R)(V/A/M/L)(A/E/K/F/M/W)KK(L/I/V)E(A/L)(F/M/L/E/I)(K/A/V/M/I/L)AD(A/V/I)E (E/R/D/K/I/A)(A/M/K/L/W)(A/F/V/K)TQ(-/G)(-/S)(-/W).
```

The inventors have designed the polypeptides of the invention to elicit neutralizing antibodies with similar specificity as Palivizumab or Motavizumab. Palivizumab is a FDA-licensed therapeutic antibody that potently neutralizes Respiratory Syncytial Virus (RSV) by binding antigenic site A (also called "site II") on the RSV F surface glycoprotein. Motavizumab is an affinity-matured variant of Palivizumab. Thus, vaccine that elicits RSV-neutralizing antibodies similar to Palivizumab (Pali) or Motavizumab (Mota) is desired to protect against RSV infection. Pali and Mota bind to a conformational epitope on the RSV F protein. As disclosed herein, the inventors have developed a computational method to design de novo protein scaffolds for epitope conformational stabilization and presentation to the immune system. This method was applied to the Mota epitope to design the polypeptides of the invention, which are shown to be monomeric, highly thermostable, and extremely high binding affinities for Mota, indicating that the polypeptides have successfully stabilized the desired epitope conformation, as confirmed by crystal structure analysis. The inventors have also demonstrated that polypeptides falling within the scope of this genus can elicit neutralizing antibodies against RSV.

Parentheses represent variable positions in the polypeptide, with the recited amino acid residues as alternatives in these positions.

In one preferred embodiment, the polypeptides comprise or consist of an amino acid sequence according to the following:

(SEQ ID NO: 2)
(-/G)(-/S)(M/L/R/F)SD(R/A/I/M/V)RKD(L/A/V)E(E/R/K/D)R(L/F/I/A)DK(L/F/A)(L/V/F)

EA(A/V/F/L)KNK(M/L/F/V)DK(F/M/E/I)KAA(M/L/F/I)RK(R/E/G/D)(G/D/P/W/Q)(Q/I/P/F)

(R/Q/K/S/H)EER(M/K/R/A)KD(W/L/M/K)(A/M/K/F)K(I/F/L/E/K/D)(A/V/M/F/L)R (D/K/Y/E)E(F/V/A/R/M)EQ(F/L/A/V/M)R(K/R)A(V/M/I)RN(F/R/V/I/Y)(L/E/A)SE(A/L)

LSKIND(Y/M/L)PITND(D/Q/K)KKL(T/I/M/V/A)SND(T/L/V/I)(K/L/I)K(F/Y/K/E/L)

(D/A/V/M)A(E/I/R)(V/A/M/L)(E/K/F/W)KK(L/I/V)E(A/L)(F/M/L/E/I)(K/A/V/M/L)A

D(A/V/I)E(E/R/D/K/I/A)(A/M/K/L/W)(A/F/V)TQ(-/G)(-/S)(-/W).

Polypeptides according to this genus are those that are present in those polypeptides demonstrating the best range of activities, as demonstrated in the examples that follow.

In a further preferred embodiment, the polypeptides comprise or consist of an amino acid sequence according to the following:

(SEQ ID NO: 3)
(-/G)(-/S)(M/L/R/F)SD(I/M)RKD(L/A)E(E/R/D)R(F/A)DK(L/F/A)(V/F)EA(A/V/L)KNK (L/F/W)DK(F/M/I)KAA(L/F/I)RK(E/G/D)(G/D/W/Q)(Q/I/P/F)(Q/K/S/H)EER(M/R/A)K

D(W/L/M)(M/K/F)K(F/L/K/D)(A/M/L)R(Y/K)E(V/A/M)EQ(L/A/M)R(K/R)A(V/M/I)R

N(F/R/I/Y)(L/E/A)SE(A/L)LSKIND(M/L)PITND(D/Q)KKL(I/M/A)SND(L/V/I)(K/L/I)

K(F/Y/E/L)(D/A/V/M)A(E/I/R)(V/A/L)(E/F/W)KK(L/I)EA(M/L/I)(K/A/M/L)AD(A/V/I)

E(R/D/I/A)(M/K/L/W)(A/F/V)TQ(-/G)(-/S)(-/W).

Polypeptides according to this genus are those that have been exemplified by the inventors as eliciting neutralizing antibodies against RSV.

In a further preferred embodiment, the polypeptides comprise or consist of an amino acid sequence selected from the group consisting of

>FFL_001
(SEQ ID NO: 4)
GSRSDMRKDAERRFDKFVEAAKNKFDKFKAALRKGDIKEERRKDMKKLA

RKEAEQARRAVRNRLSELLSKINDMPITNDQKKLMSNDVLKFAAEAEKK

IEALAADAEDKFTQGSW;

>FFL_002
(SEQ ID NO: 5)
GSLSDVRKDVEKRIDKALEAFKNKMDKEKAAFRKDPPSEERRKDKKKEF

REEREQVRKAIRNVLSEALSKINDLPITNDKKKLVSNDVIKKVAEMKKK

VELEVADVEKKVTQGSW;

>FFL_004
(SEQ ID NO: 6)
GSMSDARKDLEERLDKLLEAAKNKMDKFKAAMRKRGQREERRKKDWAKIV

RDEFEQFRKAVRNFLSEALSKINDYPITNDDKKLTSNDTKKFAAEVEKK

LEAFKADVEEAATQ;

>FFL_005
(SEQ ID NO: 7)
GSMSDIRKDLEERFDKLVEALKNKVDKMKAAFRKDQFHEERMKDWFKDL

RKEVEQMRRAVRNYASEALSKINDLPITNDDKKLASNDVLKLVAEVWKK

LEAILADVEAWFTQ;

>FFL_006
(SEQ ID NO: 8)
GSFSDIRKDAEDRADKAFEAAKNKFDKIKAAIRKDWPSEERAKDLMKKA

RYEMEQARRAIRNIESEALSKINDLPITNDQKKLASNDIIKEMARLFKK

LEALMADIEILVTQ;

and

>FFL_007
(SEQ ID NO: 9)
GSLSDIRKDAERRFDKLVEAVKNKLDKMKAALRKEGQQEERMKDLMKFM

RKEVEQLRKAMRNFLSEALSKINDMPITNDDKKLISNDLKKYDAIAEKK

LEAMKADVERMATQGSW.

Each of these polypeptides is demonstrated in the examples that follow to be monomeric, highly thermostable, and have extremely high binding affinities for Mota, indicating that the polypeptides have successfully stabilized the desired epitope conformation, and a number of these polypeptides have been shown to elicit neutralizing antibodies against RSV.

In a further preferred embodiment, the polypeptide comprises or consists of a sequence selected from the group consisting of SEQ ID NO:4 (FFL_001), SEQ ID NO:5 (FFL_002), SEQ ID NO:7 (FFL_005), SEQ ID NO:8 (FFL_006), and SEQ ID NO:9 (FFL_007). In a more preferred embodiment, the polypeptide comprises or consists of a sequence selected from the group consisting of SEQ ID NO:4 (FFL_001), SEQ ID NO:5 (FFL_002), SEQ ID NO:7 (FFL_005), and SEQ ID NO:9 (FFL_007). In a more preferred embodiment, the polypeptide comprises or consists of a sequence selected from the group consisting of SEQ ID NO:4 (FFL_001), SEQ ID NO:7 (FFL_005), and SEQ ID NO:9 (FFL_007).

In a further embodiment, the polypeptide includes any resurfaced version of the listed sequences, referring to resurfacing as described in Correia et al J. Mol Biol 2011 or any related application of the concept of resurfacing.

In a further embodiment, the polypeptide includes any variant of the listed sequences obtained by adding one or more disulfide bonds.

As disclosed herein, the inventors have developed a computational method to design protein scaffolds for epitope conformational stabilization and presentation to the immune system. This method was applied to the Mota epitope to design the polypeptides of the invention, which are shown to be monomeric, highly thermostable, and extremely high binding affinities for Mota.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may contain any suitable linker, etc. for use in any desired application, such as a peptide tag to facilitate polypeptide purification, or a T-help epitope to enhance the desired immune response. For example, two of the exemplified polypeptides discussed below include a C-terminal "GSW" to facilitate determining protein concentration, as those polypeptides did not include any other 'W' residues.

The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

In a further embodiment, the polypeptides of any embodiment of the invention may further comprise a tag, such as a detectable moiety or therapeutic agent. The tag(s) can be linked to the polypeptide through covalent bonding, including, but not limited to, disulfide bonding, hydrogen bonding, electrostatic bonding, recombinant fusion and conformational bonding. Alternatively, the tag(s) can be linked to the polypeptide by means of one or more linking compounds. Techniques for conjugating tags to polypeptides are well known to the skilled artisan. Polypeptides comprising a detectable tag can be used, for example, as probes to isolate B cells that are specific for the epitope present in the polypeptide. However, they may also be used for other detection and/or analytical purposes. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection/analysis techniques and/or methods used such as flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. When the polypeptides of the invention are used for flow cytometric detections, scanning laser cytometric detections, or fluorescent immunoassays, the tag may comprise, for example, a fluorophore. A wide variety of fluorophores useful for fluorescently labeling the polypeptides of the invention are known to the skilled artisan. When the polypeptides are used for in vivo diagnostic use, the tag can comprise, for example, magnetic resonance imaging (MRI) contrast agents, such as gadolinium diethylenetriaminepentaacetic acid, to ultrasound contrast agents or to X-ray contrast agents, or by radioisotopic labeling.

The polypeptides of the invention can also comprise a tag, such as a linker (including but not limited to an amino acid linker such as cysteine or lysine), for binding to a particle, such as a virus-like particle. As another example, the polypeptides of the invention can usefully be attached to the surface of a microtiter plate for ELISA. The polypeptides of the invention can be fused to marker sequences to facilitate purification, as described in the examples that follow. Examples include, but are not limited to, the hexa-histidine tag, the myc tag or the flag tag.

In another embodiment, a plurality of the polypeptides may be complexed to a dendrimer. Dendrimers are three dimensional, highly ordered oligomeric and/or polymeric compounds typically formed on a core molecule or designated initiator by reiterative reaction sequences adding the oligomers and/or polymers and providing an outer surface. Suitable dendrimers include, but are not limited to, "starburst" dendrimers and various dendrimer polycations. Methods for the preparation and use of dendrimers are well known to those of skill in the art.

In another embodiment, the polypeptides may be fused (via recombinant or chemical means) via their N-terminus, C-terminus, or both N- and C-termini, to an oligomerization domain. Any suitable oligomerization domain can be used. In one non-limiting embodiment, the polypeptides are fused to GCN4 variants that form trimers (hence trimers or hexamers of the fused polypeptide could be displayed). In another non-limiting embodiment, the polypeptides are fused to a fibritin foldon domain that forms trimers. In other non-limiting embodiments, the oligomerization domain could be any protein that assembles into particles, including but not limited to particles made from a (non-viral) lumazine synthase protein and particles made from (non-viral) ferritin or ferritin-like proteins.

In another embodiment, the polypeptides may be chemically conjugated to liposomes. In one non-limiting embodiment, the liposomes contain a fraction of PEGylated lipid in which the PEG groups are functionalized to carry a reactive group, and the polypeptide is chemically linked to the reactive group on the PEG. In another non-limiting embodiment, additional immune-stimulating compounds are included within the liposomes, either within the lipid layers or within the interior. In another non-limiting embodiment, specific cell-targeting molecules are included on the surface of the liposome, including but not limited to molecules that bind to proteins on the surface of dendritic cells.

In another embodiment, a plurality (ie: 2 or more; preferably at least 5, 10, 15, 20, 25, 50, 75, 90, or more copies) of the polypeptides may be present in a virus-like particle (VLP), to further enhance presentation of the polypeptide to the immune system. As used herein, a "virus-like particle" refers to a structure that in at least one attribute resembles a virus but which has not been demonstrated to be infectious. Virus-like particles in accordance with the invention do not carry genetic information encoding for the proteins of the virus-like particles. In general, virus-like particles lack a viral genome and, therefore, are noninfectious. In addition, virus-like particles can often be produced in large quantities by heterologous expression and can be easily purified. In a preferred embodiment, the VLP comprises viral proteins that may undergo spontaneous self-assembly, including but not limited to recombinant proteins of adeno associated viruses, rotavirus, recombinant proteins of norwalkvirus, recombinant proteins of alphavirus, recombinant proteins of foot and mouth disease virus, recombinant proteins of retrovirus, recombinant proteins of hepatitis B virus, recombinant proteins of tobacco mosaic virus, recombinant proteins of flock house virus, and recombinant proteins of human papillomavirus, and Qbeta bacteriophage particles. In one preferred embodiment, the viral proteins comprise hepatitis B core antigen particles. In another embodiment, the VLPs are from lipid-enveloped viruses and include lipid as well as any suitable viral protein, including but not limited to proteins from chikungunya virus, or hepatitis B surface antigen proteins. Methods for producing and characterizing recombinantly produced VLPs have been described for VLPs from several viruses, as reviewed in US 20110236408; see also U.S. Pat. No. 7,229,624. As described in the examples that follow, immunization in the context of a VLP with approximately 75 copies of the FFL_001 polypeptide (SEQ ID NO:4) conjugated onto Hepatitis B (HepB) core antigen particles results in an increased immune response to the polypeptide.

The VLPs of the invention can be used as vaccines or antigenic formulations for treating or limiting RSV infection, as discussed herein. In some embodiments, the VLPs may further comprise other scaffolds presenting other epitopes from RSVF or RSVG proteins. In other embodiments, the VLP may further comprise scaffolds presenting epitopes from additional RSV proteins, such as M, N, G, and/or SH.

In another embodiment, the polypeptides may be present on a non-natural core particle, such as a synthetic polymer, a lipid micelle or a metal. Such core particles can be used for organizing a plurality of polypeptides of the invention for delivery to a subject, resulting in an enhanced immune response. By way of example, synthetic polymer or metal core particles are described in U.S. Pat. No. 5,770,380, which discloses the use of a calixarene organic scaffold to which is attached a plurality of peptide loops in the creation of an 'antibody mimic', and U.S. Pat. No. 5,334,394 describes nanocrystalline particles used as a viral decoy that are composed of a wide variety of inorganic materials, including metals or ceramics. Preferred metals in this embodiment include chromium, rubidium, iron, zinc, selenium, nickel, gold, silver, platinum. Preferred ceramic materials in this embodiment include silicon dioxide, titanium dioxide, aluminum oxide, ruthenium oxide and tin oxide. The core particles of this embodiment may be made from organic materials including carbon (diamond). Preferred polymers include polystyrene, nylon and nitrocellulose. For this type of nanocrystalline particle, particles made from tin oxide, titanium dioxide or carbon (diamond) are particularly preferred. A lipid micelle may be prepared by any means known in the art. See U.S. Pat. No. 7,229,624 and references disclosed therein.

In a second aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a third aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a fourth aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the man skilled in the art.

In a fifth aspect, the present invention provides pharmaceutical compositions (such as a vaccine), comprising one or more polypeptides, VLPs, nucleic acids, recombinant expression vectors, or host cells of the invention and a pharmaceutically acceptable carrier. The pharmaceutical compositions of the invention can be used, for example, in the methods of the invention described below. The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides may be the sole active agent in the pharmaceutical composition, or the composition may further comprise one or more other agents suitable for an intended use, including but not limited to adjuvants to stimulate the immune system generally and improve immune responses overall. Any suitable adjuvant can be used. The term "adjuvant" refers to a compound or mixture that enhances the immune response to an antigen. Exemplary adjuvants include, but are not limited to, Adju-Phos, Adjumer™, albumin-heparin microparticles, Algal Glucan, Algammulin, Alum, Antigen Formulation, AS-2 adjuvant, autologous dendritic cells, autologous PBMC, Avridine™ B7-2, BAK, BAY R1005, Bupivacaine, Bupivacaine-HCl, BWZL, Calcitriol, Calcium Phosphate Gel, CCR5 peptides, CFA, Cholera holotoxin (CT) and Cholera toxin B subunit (CTB), Cholera toxin A1-subunit-Protein A D-fragment fusion protein, CpG, CRL1005, Cytokine-containing Liposomes, D-Murapalmitine, DDA, DHEA, Diphtheria toxoid, DL-PGL, DMPC, DMPG, DOC/Alum Complex, Fowlpox, Freund's Complete Adjuvant, Gamma Inulin, Gerbu Adjuvant, GM-CSF, GMDP, hGM-CSF, hIL-12 (N222L), hTNF-alpha, IFA, IFN-gamma in pcDNA3, IL-12 DNA, IL-12 plasmid, IL-12/GMCSF plasmid (Sykes), IL-2 in pcDNA3, IL-2/Ig plasmid, IL-2/Ig protein, IL-4, IL-4 in pcDNA3, Imiquimod, ImmTher™, Immunoliposomes Containing Antibodies to Costimulatory Molecules, Interferon-gamma, Interleukin-1 beta, Interleukin-12, Interleukin-2, Interleukin-7, ISCOM(s)™, Iscoprep 7.0.3™, Keyhole Limpet Hemocyanin, Lipid-based Adjuvant, Liposomes, Loxoribine, LT(R192G), LT-OA or LT Oral Adjuvant, LT-R192G, LTK63, LTK72, MF59, MONTANIDE ISA 51, MONTANIDE ISA 720, MPL™, MPL-SE, MTP-PE, MTP-PE Liposomes, Murametide, Murapalmitine, NAGO, nCT native Cholera Toxin, Non-Ionic Surfactant Vesicles, non-toxic mutant E112K of Cholera Toxin mCT-E112K, p-Hydroxybenzoique acid methyl ester, pCIL-10, pCIL12, pCM-VmCAT1, pCMVN, Peptomer-NP, Pleuran, PLG, PLGA, PGA, and PLA, Pluronic L121, PMMA, PODDS™, Poly rA: Poly rU, Polysorbate 80, Protein Cochleates, QS-21, Quadri A saponin, Quil-A, Rehydragel HPA, Rehydragel LV, RIBI, Ribilike adjuvant system (MPL, TMD, CWS), S-28463, SAF-1, Sclavo peptide, Sendai Proteoliposomes, Sendai-containing Lipid Matrices, Span 85, Specol, Squalane 1, Squalene 2, Stearyl Tyrosine, Tetanus toxoid (TT), Theramide™, Threonyl muramyl dipeptide (TMDP), Ty Particles, and Walter Reed Liposomes. Selection of an adjuvant depends on the subject to be vaccinated. Preferably, a pharmaceutically acceptable adjuvant is used.

Compositions comprising the polypeptides can be stored in any standard form, including, e.g., an aqueous solution or a lyophilized cake. Such compositions are typically sterile when administered to cells or subjects. Sterilization of an aqueous solution is readily accomplished by filtration through a sterile filtration membrane. If the composition is stored in lyophilized form, the composition can be filtered before or after lyophilization and reconstitution.

In a sixth aspect, the present invention provides methods for treating and/or limiting an RSV infection, comprising administering to a subject in need thereof a therapeutically effective amount of one or more polypeptides of the invention, salts thereof, conjugates thereof, VLPs thereof, or pharmaceutical compositions thereof, to treat and/or limit the RSV infection. In another embodiment, the method comprises eliciting an immune response in an individual having or at risk of an RSV infection, comprising administering to a subject in need thereof a therapeutically effective amount of one or more polypeptides of the invention, salts thereof, conjugates thereof, VLPs thereof, or pharmaceutical compositions thereof, to generate an immune response.

"Respiratory Syncytial Virus" and "RSV" refer to a negative-sense, single-stranded RNA virus of the family Paramyxoviridae that causes a respiratory disease, especially in children.

When the method comprises treating an RSV infection, the one or more polypeptides, VLPs, or compositions are administered to a subject that has already been infected with the RSV, and/or who is suffering from symptoms (including but not limited to lower respiratory tract infections, upper respiratory tract infections, bronchiolitis, pneumonia, fever, listlessness, diminished appetite, recurrent wheezing, and asthma) indicating that the subject is likely to have been infected with the RSV. As used herein, "treat" or "treating" means accomplishing one or more of the following: (a) reducing RSV titer in the subject; (b) limiting any increase of RSV titer in the subject; (c) reducing the severity of RSV symptoms; (d) limiting or preventing development of RSV symptoms after infection; (e) inhibiting worsening of RSV symptoms; (f) limiting or preventing recurrence of RSV symptoms in subjects that were previously symptomatic for RSV infection. In one embodiment method, polypeptides, VLPs, or compositions are used as "therapeutic vaccines" to ameliorate the existing infection and/or provide prophylaxis against infection with additional RSV virus.

When the method comprises limiting an RSV infection, the one or more polypeptides, VLPs, or compositions are administered prophylactically to a subject that is not known to be infected, but may be at risk of exposure to the RSV. As used herein, "limiting" means to limit RSV infection in subjects at risk of RSV infection. Groups at particularly high risk include children under age 18 (particularly infants 3 years or younger), adults over the age of 65, and individuals suffering from any type of immunodeficiency. In this method, the polypeptides, VLPs, or compositions are used as vaccines.

As used herein, a "therapeutically effective amount" refers to an amount of the polypeptide that is effective for treating and/or limiting RSV infection. The polypeptides are typically formulated as a pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Polypeptide compositions may also be administered via microspheres, liposomes, immune-stimulating complexes (ISCOMs), or other microparticulate delivery systems or sustained release formulations introduced into suitable tissues (such as blood). Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In certain embodiments, the polypeptides of the invention neutralize RSV infectivity, as demonstrated in the examples that follow. In various embodiments, the polypeptides of the invention prevent RSV from infecting host cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to infection of host cells by RSV in the absence of the polypeptides. Neutralization can be measured using standard techniques in the art.

In another aspect, the present invention provides pharmaceutical composition, comprising (a) isolated nucleic acids, recombinant expression vectors, and/or recombinant host cells of the invention; and (b) a pharmaceutically acceptable carrier. In this aspect, the nucleic acids, expression vectors, and host cells of the invention can be used as polynucleotide-based immunogenic compositions, to express an encoded polypeptide in vivo, in a subject, thereby eliciting an immune response against the encoded polypeptide. Various methods are available for administering polynucleotides into animals. The selection of a suitable method for introducing a particular polynucleotide into an animal is within the level of skill in the art. Polynucleotides of the invention can also be introduced into a subject by other methods known in the art, e.g., transfection, electroporation, microinjection, transduction, cell fusion, DEAE dextran, calcium phosphate precipitation, lipofection (lysosome fusion), or a DNA vector transporter (see, e.g., Wu et al. (1992) J. Biol. Chem. 267:963-967).

The immune response against the polypeptides, VLPs, or compositions of the invention can be generated by one or more inoculations of a subject with an immunogenic composition of the invention. A first inoculation is termed a "primary inoculation" and subsequent immunizations are termed "booster inoculations". Booster inoculations generally enhance the immune response, and immunization regimens including at least one booster inoculation are preferred. Any polypeptide, VLP, or composition of the invention may be used for a primary or booster immunization. The adequacy of the vaccination parameters chosen, e.g., formulation, dose, regimen and the like, can be determined by taking aliquots of serum from the subject and assaying antibody titers during the course of the immunization program. Alternatively, the T cell populations can by monitored by conventional methods. In addition, the clinical condition of the subject can be monitored for the desired effect, e.g., limiting RSV infection, improvement in disease state (e.g., reduction in viral load), etc. If such monitoring indicates that vaccination is sub-optimal, the subject can be boosted with an additional dose of composition, and the vaccination parameters can be modified in a fashion expected to potentiate the immune response. Thus, for example, the dose of the polypeptide, VLP, or composition, and/or adjuvant, can be increased or the route of administration can be changed.

In a further aspect, the present invention provides methods for monitoring an RSV-induced disease in a subject and/or monitoring response of the subject to immunization by an RSV vaccine, comprising contacting the polypeptides, the VLPs, or the pharmaceutical compositions of the invention with a bodily fluid from the subject and detecting RSV-binding antibodies in the bodily fluid of the subject. By "RSV-induced disease" is intended any disease caused, directly or indirectly, by RSV. The method comprises contacting a polypeptide, VLP, or composition of the invention with an amount of bodily fluid (such as serum, whole blood, etc.) from the subject; and detecting RSV-binding antibodies in the bodily fluid of the subject. The detection of the RSV binding antibodies allows the RSV disease in the subject to be monitored. In addition, the detection of RSV binding antibody also allows the response of the subject to immunization by an RSV vaccine to be monitored. In still other methods, the titer of the RSV binding antibodies is determined. Any suitable detection assay can be used, including but not limited to homogeneous and heterogeneous binding immunoassays, such as radioimmunoassays (RIA), ELISA, immunofluorescence, immunohistochemistry, FACS, BIA-CORE and Western blot analyses. The methods may be carried in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape. The polypeptides of the invention for use in this aspect may comprise a conjugate as disclosed above, to provide a tag useful for any detection technique suitable for a given assay.

In a still further aspect, the present invention provides methods for detecting RSV binding antibodies, comprising (a) contacting the polypeptides, the VLPs, or the compositions of the invention with a composition comprising a candidate RSV binding antibody under conditions suitable for binding of RSV antibodies to the polypeptide, VLP, or composition; and (b) detecting RSV antibody complexes with the polypeptide, VLP, or composition. In this aspect, the methods are performed to determine if a candidate RSV binding antibody recognizes the RSV F epitope present in the polypeptides of the invention. Any suitable composition may be used, including but not limited to bodily fluid samples (such as serum, whole blood, etc.) from a suitable subject (such as one who has been infected with RSV), naive libraries, modified libraries, and libraries produced directly from human donors exhibiting an RSV-specific immune response. The assays are performed under conditions suitable for promoting binding of antibodies against the polypeptides; such conditions can be determined by those of skill in the art based on the teachings herein. Any suitable detection assay can be used, including but not limited to homogeneous and heterogeneous binding immunoassays, such as radioimmunoassays (RIA), ELISA, immunofluorescence, immunohistochemistry, FACS, BIACORE and Western blot analyses. The methods may be carried in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape. The polypeptides of the invention for use in this aspect may comprise a conjugate as disclosed above, to provide a tag useful for any detection technique suitable for a given assay. In a further embodiment, the RSV F-binding antibodies are isolated using standard procedures. In one embodiment, the methods may comprise isolation of polypeptide-specific memory B cells by fluorescence activated cell sorting (FACS) using standard techniques in the art (see, for example, *Science* DOI: 10.1126/science. 1187659)

In another aspect, the present invention provides methods for producing RSV antibodies, comprising (a) administering to a subject an amount effective to generate an antibody response of the polypeptides, the VLPs, and/or the compositions of the invention; and (b) isolating antibodies produced by the subject.

The polypeptides of the invention can also be used to generate antibodies that recognize the polypeptides of the invention. The method comprises administering to a subject a polypeptide, VLP, or composition of the invention. Such antibodies can be used, for example, in RSV research. A subject employed in this embodiment is one typically employed for antibody production, including but not limited to mammals, such as, rodents, rabbits, goats, sheep, etc. The antibodies generated can be either polyclonal or monoclonal antibodies. Polyclonal antibodies are raised by injecting (e.g. subcutaneous or intramuscular injection) antigenic polypeptides into a suitable animal (e.g., a mouse or a rabbit). The antibodies are then obtained from blood samples taken from the animal. The techniques used to produce polyclonal antibodies are extensively described in the literature. Polyclonal antibodies produced by the subjects can be further purified, for example, by binding to and elution from a matrix that is bound with the polypeptide against which the antibodies were raised. Those of skill in the art will know of various standard techniques for purification and/or concentration of polyclonal, as well as monoclonal, antibodies. Monoclonal antibodies can also be generated using techniques known in the art.

In a seventh aspect, the present invention provides computational methods for designing a polypeptide scaffold. Such a method may include:

(a) defining a polypeptide structural motif to be used as a folding nucleus;

(b) defining (i) a target three-dimensional topology for a polypeptide scaffold compatible with the polypeptide structural motif and (ii) a region of the target three-dimensional topology to be replaced by the polypeptide structural motif;

(c) growing an extended polypeptide chain from termini of atomic coordinates of the polypeptide structural motif;

(d) folding the extended polypeptide chain while maintaining backbone dihedral angles of the polypeptide structural motif fixed; and (e) identifying folded polypeptide chains that meet a user-defined threshold of polypeptide backbone root mean square deviation (rmsd) relative to the target three-dimensional topology as polypeptide scaffolds of interest.

The disclosed computational methods may be carried out by any suitable computing device, including but not limited to a server computer, a personal computer, and/or a mobile computer for instance.

The polypeptide scaffolds designed via the disclosed computational methods may be used, for example, to promote epitope conformational stabilization and presentation to the immune system. The starting points for the methodology (referred to herein as Fold From Loops (FFL)) are a structural motif responsible for conferring functionality to the protein and a target topology to be folded around the functional motif (FIG. 1). The practical advances of the FFL approach are two-fold: (1) the in silico folding stage will allow for the optimization of the whole scaffold structure and sequence to stabilize the precise conformation of the functional motif; and (2) for the target topology, the strategy is capable of utilizing either naturally occurring folds or folds not yet observed in nature. The method may be applied to fold and design a three-helical bundle topology around a RSV broadly neutralization epitope, as discussed in more detail below.

The polypeptide structural motif can be any functional polypeptide segment or domain, including but not limited to protein binding sites, enzyme active sites, small molecule binding sites, DNA or RNA binding sites, etc. Similarly, the structural motif can be a continuous structural motif (a single amino acid segment) for use as a folding nucleus, or may comprise multiple (i.e., 2 or more) disconnected segments to be displayed in a specific three-dimensional geometry.

The feature of defining the polypeptide structural motif to be used as a folding nucleus may take various forms. In one example, the computer device may define the polypeptide structural motif based on data input by a user, data retrieved from local and/or remote data storage, and/or data received from another computing device. Other examples are possible as well.

The feature of defining the target three-dimensional topology for a polypeptide scaffold compatible with the polypeptide structural motif and the region of the target three-dimensional topology to be replaced by the polypeptide structural motif may also take various forms. In one example, the computer device may define the target three-dimensional topology and the region to be replaced based on data input by a user, data retrieved from local and/or remote data storage, and/or data received from another computing device. In turn, the data in which the target three-dimensional topology is based may take various forms. For example, this data may indicate any suitable features for an intended use, including but not limited to (i) pre-existing three-dimensional similarity with the structural motif in terms of atomic coordinates, (ii) pre-existing similarity with the structural motif in terms of secondary structure, and/or (iii) a comparison of the distances between the termini of the motif and the distances between residues in the topology that are intended to be separated by similar distances. Other examples are possible as well.

The computing device may also take into account various constraints in defining the target three-dimensional topology. For example, the computing device may consider structural fragments, from proteins or models of known structure, which include backbone dihedral angle information and which are selected as consistent with the target topology according to sequence and/or secondary structure similarity. In particular, the computing device may randomly apply the set of dihedral angles included in these fragments to the polypeptide chain. As another example, the computing device may use distance restraints that are collected from a either a low or high resolution three-dimensional structure to guide the FFL folding stage by energetically penalizing polypeptide conformations on which the distances between particular pairs of residues are not within the corresponding distances of the target topology +/− a user-defined standard deviation. Other examples are possible as well.

The defined region of the target three-dimensional topology to be replaced by the polypeptide structural motif may take various forms. In one embodiment, the region is a continuous structural motif (a single amino acid segment). In another embodiment, the region comprises multiple (i.e., 2 or more) disconnected segments.

In one embodiment, the method further comprises determining one or more constraints from the target three-dimensional topology prior to growing the extended polypeptide chain. These constraints may take various forms, including but not limited to $C_\alpha$ distance constraints, constraints on angles or dihedrals involving $C_\alpha$ or other coordinates, geometrical constraints based on disulfide bonds or metal-binding sites thought to be important to stabilize the topology, constraints on interactions between specific secondary structural elements (e.g., if a topology has several helices a constraint on which helix should pair with which other helix, or if there are beta sheets in the topology, constraints on which beta strands should be pairing with other beta strands in the beta sheet), and/or constraints on which residues should be buried and which should be exposed (e.g., by estimating the number of $C_\beta$ neighbors during folding or more precisely by the accessible surface area). In one embodiment, the constraints may comprise determining $C_\alpha$ distance constraints from the target three-dimensional topology. In one non-limiting example, distances between the $C_\alpha$ atoms of residues with a sequence separation larger than 6 are collected outside the range where the binding site will be inserted.

The feature of growing the extended polypeptide chain from termini of atomic coordinates of the polypeptide structural motif may further take various forms. For example, the computing device may use the backbone coordinates of the polypeptide structural motif to serve as a "folding nucleus", from the termini of which an extended chain is initially grown and subsequently folded. In this respect, the exact backbone atomic coordinates of the motif are preferably conserved throughout the method. The computing device may also use the target three-dimensional topology as a template to extract $C_\alpha$ distances, which it may then use as restraints to guide the folding stage. In one non-limiting embodiment, the computing device may grow an extended polypeptide chain from the termini of the binding site atomic coordinates, which can result in a centroid structure in which the polypeptide structural motif contains its original backbone dihedral angles but all remaining residues are in an extended conformation. Other examples are possible as well.

The feature of folding the extended polypeptide chain while maintaining backbone dihedral angles of the polypeptide structural motif fixed may also take various forms. In particular, the computing device may use any suitable folding protocol to carry out this feature, including but not limited to the protocols available in the ROSETTA™ software package (Bradley P, Baker D. Proteins. 2006 Dec. 1; 65(4):922-9; Simons K T, Kooperberg C, Huang E, Baker D. J Mol Biol. 1997 Apr. 25; 268(1):209-25.; Rohl C A, Strauss C E, Misura K M, Baker D. Methods Enzymol. 2004; 383:66-93.). For example, the computing device may use the ROSETTA™ abinitio protocol that relies on fragment insertion to search for low energy conformations evaluated by a low-resolution energy function. Optionally, the computing device may use a folding protocol based on distance restraints. For the FFL protocol, structural fragments from existing proteins were selected according to sequence similarity and secondary structure prediction. The sequence assigned to the low-resolution models in FFL was taken from the target topology and the input structural motif.

While folding the extended polypeptide chain, the computing device keeps backbone dihedral angles of the structural motif fixed to act as a "folding nucleus". While the C-alpha distances collected from the target topology can be used to restrain the conformational sampling, $C_\alpha$ distance-based constraints can be relaxed, for example, by allowing a larger standard deviation in a Gaussian penalty function.

Since the methods can be used with discontinuous structural motifs with 2 or more disconnected segments, in addition to holding fixed the backbone dihedral angles within the polypeptide structural motif, the method may further comprise holding fixed the spatial arrangement of segments in the structural motif.

The feature of identifying extended polypeptide chains that meet a user-defined threshold of polypeptide backbone rmsd relative to the target three-dimensional topology as polypeptide scaffolds of interest may take various forms as well. For example, the computing device may identify structures with a backbone rmsd less than a user-defined threshold relative to the target topology can be selected for the subsequent full atom design stage. In this respect, the user-defined threshold may be, for example, 5 angstroms. Other examples are possible as well.

In a preferred embodiment, the methods further comprise recovering original side chain conformations within the structural motif and performing several (at least 1, 3, 4, 5, 6, 7, 8, 9, 10, or more) cycles of iterative folding design. In this embodiment, some or all of the original side-chain conformations of the structural motif are recovered and kept fixed throughout the rounds of iterative design and full-atom optimization. Some positions on the structural motif can be allowed to change residues to other amino acids. For example in one embodiment, positions on the structural motif would be allowed to change residues to any of the 20 amino acids if the original side-chains do not contribute directly to function (e.g. do not directly contact a binding partner such as an antibody or small molecule or DNA or RNA, etc., and do not catalyze a chemical reaction) and if other side-chains at those positions may make direct contact with other parts of the folded scaffold and in that way may contribute to conformational stabilization of the structural motif and thermal stability of the scaffold. The models generated in the folding step are typically subjected to several rounds of sequence design paired with local backbone optimization throughout the structure. Residues outside of the structural motif are allowed to change to any of the 20 amino-acids, though the user may restrict the allowed amino acids at certain positions as is common and well known to those skilled in the art of protein design. For example the user may choose to disallow the inclusion of cysteine residues if the designed protein is intended for use in oxidizing environments such as the extracellular environment. In one embodiment, a user of the FFL design method can decide how many full atom designs should be created. For example, a reasonable number would be 10000; however, a smaller or larger number of designs could be appropriate. The method can further include employing one or more score filters (such as full atom score, packing, buried unsatisfied polar atoms or other filters) and selecting desirable (e.g., based on specified criteria) designs for manual inspection. The number of designs for inspection can be determined by the user. For example, a user could inspect 50 designs; however, one of ordinary skill in the art will recognize that the number of designs inspected by the user could be lesser or greater than 50 designs.

In another embodiment, the method may also comprise filtering the designs further according to one or more structural features including but not necessarily limited to ROSETTA™ energy, Ramachandran score, number of buried unsatisfied backbone atoms, and core packing. In this embodiment, the final pool of designed models (typically 10000) is filtered and ranked according to these structural criteria.

In still another embodiment, the method may further comprise redesigning of surface residues of the initial topology (not the target binding site), for example, to eliminate clusters of hydrophobic residues if present. The method may also further comprise redesigning structure at selected positions in the protein core, for example, to mutate overrepresented residues, improve packing, and/or eliminate buried polar amino acids. In one embodiment, the redesigning steps can be followed by a step of full-atom optimization. In some embodiments, the method can include an additional filtering step based on energy, packing and visual inspection. The method may further comprise maintaining some or all of the amino acids on the surface of the scaffolds outside the structural motif the same as in the target topology, which may impose similarities in amino acid positions between different polypeptide designs.

In yet another embodiment, the method may additionally include storing data representing the defined polypeptide structural motif, the defined target three-dimensional topology, the defined region of the target three-dimensional topology, the identified extended polypeptide chains, the one or more constraints, and/or any of the other features discussed herein. Further, the method may include displaying data representing the defined polypeptide structural motif, the defined target three-dimensional topology, the defined region of the target three-dimensional topology, and/or the identified folded polypeptide chains. Further yet, the method may include sending, to another computing device, data representing the defined polypeptide structural motif, the defined target three-dimensional topology, the defined region of the target three-dimensional topology, and/or the identified folded polypeptide chains.

The computing device that carries out the disclosed methods may take various forms. An exemplary computing device may include a user interface, a communication interface, a processor, and data storage, all linked together via a system bus, network, or other connection mechanism. The computing device may include other components as well.

The user interface may be configured to facilitate user interaction with computing device. As such, user interface may include or provide connectivity to various components that facilitate user interaction. For example, user interface may include or provide connectivity to input components such as a keyboard, a mouse, touch screen, and/or a microphone for instance. As another example, user interface may include or provide connectivity to output components such as a display screen and/or a speaker for instance. As yet another example, user interface may include signal-processing components such as analog-to-digital (A-D) and/or digital-to-analog (D-A) circuitry. Other configurations are possible as well.

The communication interface may be configured to facilitate communication with another computing device. To facilitate this communication, communication interface may take various forms. For example, communication interface may take the form of an Ethernet interface, a serial bus interface (e.g., Firewire, USB 2.0, etc.), a chipset and antenna adapted to facilitate wireless communication according a desired protocol, and/or any other interface that provides for wired and/or wireless communication with another computing device. Communication interface may also include some combination of different interfaces types. Other configurations are possible as well.

The processor may comprise one or more processor components, such as general-purpose processors (e.g., a microprocessor), application-specific processors (e.g., an ASIC or DSP), programmable logic devices (e.g., an FPGA), or other processor components now known or later developed. Data storage, in turn, may comprise one or more non-transitory computer-readable storage mediums, such as volatile data storage mediums (e.g., RAM) registers, and/or cache) and/or non-volatile data storage mediums (e.g., ROM, a hard disk drive, a solid state drive, flash memory, an optical storage device, and/or a floppy disk). Some storage mediums may be integrated in whole or in part with the processor. Further, some storage mediums may be external to and/or removable from computing device, in which case such storage mediums may interface with computing device in various manners (e.g., via a peripherals interface and/or communication interface). Data storage may contain (i) program logic and (ii) program data, which may be maintained either separately or together within data storage.

Program logic preferably comprises machine-language instructions that are executable and/or interpretable by a processor, such as processor, to carry out functions in accordance with the disclosed methods for designing polypeptide scaffolds. In turn, program data may contain data that may be used by processor in connection with the disclosed methods for designing polypeptide scaffolds, such as data representing the defined polypeptide structural motif, the defined target three-dimensional topology, the defined region of the target three-dimensional topology, the identified folded polypeptide chains, the one or more constraints, and/or the user-defined threshold for instance.

The method may further comprise redesigning of surface residues of the initial topology (not the target binding site), for example, to eliminate clusters of hydrophobic residues if present. The method may also further comprise redesigning structure at selected positions in the protein core, for example, to mutate overrepresented residues, improve packing, and/or eliminate buried polar amino acids. In one embodiment, the redesigning steps can be followed by a step of full-atom optimization. In some embodiments, the method can include an additional filtering step based on energy, packing and visual inspection.

In another aspect, the present invention provides a non-transitory machine readable storage medium, comprising a set of instructions for causing a computing device to carry out the computational methods of the invention. In this aspect, the invention provides a machine readable storage medium that comprises instructions for causing a processor to execute automated computational method steps for designing polypeptide scaffolds. As used herein the term "computer readable storage medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Example 1

Fold from Loops

The FFL protocol was implemented in the ROSETTA™ software package. The FFL protocol requires as starting inputs a structural motif and a pdb file of the target topology to be folded (FIG. 1). Here, the input structural motif was the RSV peptide-epitope, which has been crystallized in complex with the Fab portion of Motavizumab (PDBid 3IXT). The 3-helix bundle target topology was selected based on the following criteria: the existence of a helix-turn-helix motif in the helical bundle; the high thermal stability of the protein used as the template target topology. The FFL protocol can be partitioned in two-main stages: I) a low-resolution stage with large conformational sampling; II) a full-atom stage with iterations of sequence design and confined conformational sampling.

Low-Resolution Conformational Sampling

Extended polypeptide chains were appended to the termini of the input motif such that the total number of residues matches that of the template topology. The residues of the topology onto which the input motif were inserted were defined through a loop file; the location of the input motif determined the length of the polypeptide chains to append. At this low-resolution stage the representation of the polypeptide chain was coarse-grained; only the atoms of the main chain were explicitly represented and the side chains were represented as spheres.

The conformational sampling carried out at this stage was performed with a Rosetta™ abinitio type protocol. The abinitio protocol relies on the insertion of fragments extracted from a large set of know protein structures. The used fragments were collected with the program NNMAKE™, which builds fragment libraries according to a provided sequence and its secondary structure prediction. For the design work described here the fragments were derived from the sequence of the template.

Optionally, to bias the folding trajectory towards similar structures to that of the target topology, C alpha restraints are extracted [Rohl et al., Methods in Enzymology 383 (2004)] from the target topology and incorporated as a scoring term in the overall scoring function. The Rosetta™ folding protocol which incorporates distance restraints has been previously described by Rohl et al. The distances between residues were collected if sequence separation was larger than 6 and if both residues were outside of the range of the functional site including five residues upstream and downstream. For the designs described here, a standard deviation of 3 Å for each $C\alpha$-$C\alpha$ distance extracted from the template protein was allowed.

In general, throughout the sampling stages the backbone dihedral angles of the input motif were untouched; nevertheless the algorithm implementation allows setting the termini of the motif as moveable. The rationale to allow for these degrees of freedom within the input motif is to favor smooth structural transitions between the input motif and the remaining protein.

Full-Atom Sequence Design and Structural Optimization

After the low-resolution stage during which a large conformational space was explored, the generated models were filtered according to their RMSD relative to the coordinates of native topology. Here, an RMSD threshold of 5 Å was used such that models in the structural vicinity of the target topology would be carried to the sequence design stage, in case a model was above the defined threshold it was automatically discarded. The original side-chain conformations, from the input motif, were recovered and kept fixed throughout the full-atom stage.

By default, in the sequence design stage the 19 amino-acids (cysteine excluded) were allowed in every residue of the models excluding the input functional motif. The exclusion of cysteine is not required. Generally, cysteines are not used for immunogen design unless disulfide bonds are being designed, since immunogens are intended for the extracellular environment which is oxidizing and hence unpaired cysteines in the extracellular environment will tend to form disulfides by paring with other cysteines. For protein design related to intracellular applications, unpaired cysteines are perfectly acceptable. Also at this stage, additional options were implemented for a finer control of the amino-acid identities allowed in particular residue positions. In the FFL designs described here, some positions of the input motif were not part of the antibody-contacting surface and therefore constituted part of the protein core; in some simulations the non contacting side-chains were allowed to change.

After each step of sequence design, a step of full-atom refinement (relax) was performed ensuring that the local conformational space was explored. The relax protocol is composed of several rounds of: small backbone perturbations; side-chain repacking; and energy minimization.

The cycles of iterative sequence design and structural minimization were repeated 3 times. The number of cycles is adjustable by the user.

Design Selection

Quality Filters

Typically 10,000 designs were generated by each FFL run, the first filter applied was based on Rosetta™ full-atom energy, and the best 50 designs by Rosetta Energy™ were further considered. Next, a composite filter was applied to select designs with the best structural features. The structural features considered were: Ramachandran score as implemented in Rosetta™; counts of buried polar atoms not involved in hydrogen bonds; and core packing assessment according to the RosettaHoles™ algorithm. Designed models within the top-25 according to the three features were taken to the next stage.

Some of the designs were selected according the geometrical properties of the models, in particular the bend angle of the helices. Statistics of the bend angles of each helix that composed the helical bundles were collected with the software Helanal™. Bundles with the lowest average bend angle were selected for next stage.

Post-FFL Design

A long identified culprit of the Rosetta™ energy function is the notorious inability to accurately design solvent exposed residues; one of the possible causes is related with the absence of appropriate electrostatics parameterization. To circumvent this known culprit, the first step of post-FFL design was to impose identical residues in the solvent exposed positions as those of the protein used as the template topology.

Next, a step of manual design and all-atom refinement was employed to correct core-packing defects and remove polar amino acids from the core. The manual design was performed to: correct the occurrence of polar residues (in particular histidines) in the designs' cores; and designs straight from the automated stage having alanines overrepresented and valines underrepresented when compared to the template topology. The high frequency of alanines is likely related to the energy term which represents the probability of finding a certain amino-acid given the dihedral angles of the backbone (Ramachandran term), given that the FFL proteins where mostly helical the Ramachandran term will favor the occurrence of alanines and disfavor valines or amino-acids with beta branched side-chains; another potential influencing factor is the proximal arrangement of the helices which in some positions might not allow to fit amino acids larger than alanine.

Given the nature of the iterative design procedure the generated models were highly intolerable to mutations in the core. Consequently, in the manual design stage, steric clashes were introduced by the mutations and a refinement step was necessary for accurate evaluation of the full-atom energies. The refinement served also as a filtering step to the performed manual mutations, as a given mutation or set of mutations would only be accepted if the full atom energy would recover significantly without causing major distortions in the helical local structure. One of the designs (FFL_001) selected for experimental characterization was a straight FFL design with no manual changes performed in the core. This polypeptide was thermodynamically stable and bound the antibody of interest with high affinity.

The designs selected for experimental characterization differed by 6 to 48 mutations when compared to each other. When compared to the sequence of the original template the designs showed between 51 and 59 mutations. A sequence alignment of the FFL designs and the sequence of the original template is shown in FIG. 3.

The backbone rmsds within the designed models were of 0.53 to 3.06 Å and between 1.83 and 2.91 when the designs are compared to the coordinate of the initial template.

Design Minimization

To further reduce the size of the FFL designs, protein segments that didn't contact the mota epitope were eliminated.

Experimental Methods

Expression and Purification

Non-Labeled Protein

DNA segments encoding scaffold constructs were synthesized with optimized codon usage and RNA structure (Codon Devices, Genscript Corp.), subcloned into pET29 (EMD Biosciences) and transformed into Arctic Express™ *E. coli* (Invitrogen). Single colonies were grown overnight at 37° C. in 10 mL Luria Broth (LB) plus Kanamycin (100 mg/ml). The starter cultures were expanded into 1 L of LB plus Kanamycin and incubated at 37° C.; when cells reached log phase, 250 μM of IPTG was added to the cultures to induce protein expression and the cells were then incubated overnight at 12° C. Cultures were then pelleted and resuspended in start buffer (160 mM Imidazole, 4 M Sodium Chloride, 160 mM Sodium Phosphate), a tablet of protease inhibitor (Novagen) was added and the cell suspension was frozen at −20° C.

The cell suspension was thawed and 10 ml of 10× Bugbuster™ (Novagen), 50 μL of Benzonase Nucleases and 1.7 μL of rLysozyme (Novagen) were added to lyse the cells; the cell suspension was then gently tumbled in an orbital shaker for 20 minutes. Lysed cells were pelleted and the supernatant was filtered through a 0.22 μm filter (Millipore). Supernatants were tumbled with 5 mL of Ni++ Sepharose 6 Fast Flow (GE Healthcare) for 1 hour at 4° C. The resin was washed 3 times with 30 mL wash buffer (50 mM imidazole, 500 mM Sodium Chloride and 160 mM Sodium Phosphate) and eluted with 20 mL of Elution Buffer (250 mM Imidazole, 500 mM Sodium Chloride and 20 mM Sodium Phosphate). Fractions containing the construct of interest were combined and further purified by preparative size exclusion chromatography (SEC) on Superdex 75 16/60 (GE Healthcare) at room temperature in HBS. Collected fractions were analyzed on a 4-12% SDS denaturing gel (Invitrogen) and positive fractions were combined and concentrated by ultrafiltration (Vivaspin, Bioexpress). Protein concentration was determined by measuring UV absorption signal at 280 nm (Nanodrop™) and calculated from the theoretical extinction coefficient. To facilitate a rapid and accurate protein quantification the sequence GSW was added to all the designs without tryptophans in their primary sequence.

Low-Endotoxin Protein

In order to prepare low-endotoxin protein for immunization studies, bacterial pellets were alternately resuspended in detergent buffer (50 mM NaH2PO4, 500 mM NaCl, 10 mM imidazole, 0.5 mg/ml lysozyme, 0.01 mg/ml DNase, 0.1% Triton X114) and Ni++ resin was alternately initially washed in 10 mM imidazole, 50 mM NaH2PO4, 500 mM NaCl, 0.1% Triton X114.

N15-Labeled Protein

Isotopically labeled samples of FFL_001, FFL_005, FFL_006 and FFL_007 were grown in minimal MOPS medium supplemented with 1 g/L of $^{15}$N ammonium chloride. The starter cultures were expanded to 1 L of MOPS and were incubated overnight at 37° C.; 3 ml of 40% $^{15}$N glucose was added to continue growth, upon reaching an $OD_{\lambda=600}$ 250 μM of IPTG was added to the cultures to induce protein expression and the cells were then incubated overnight at 16° C.

Light Scattering

The monodispersivity and molecular weight of purified proteins were further assessed by HPLC (Agilent, 1200 series) coupled in-line to a static light scattering device (miniDAWN TREOS, Wyatt). 100 μl of 1-2 mg/mL protein sample was used and the collected data was analyzed with the ASTRA™ software (Wyatt).

Circular Dichroism

Solution thermostabilities ($T_m$) were determined by circular dichroism (CD) on an Aviv 62A DS spectrometer. Far-UV wavelength scans (190-260 nm) of 15 to 25 μM protein were collected in a 1 mm path length cuvette. Temperature-induced protein denaturation was followed by change in ellipticity at 210 nm. Experiments were carried over a temperature range from 1-99° C., with 2° C. increments every 3 minutes, and the resulting data was converted to mean residue ellipticity and fitted to a two-state model.

NMR

NMR samples were prepared in 25 mM sodium phosphate, 150 mM NaCl, pH 7.0, and 90% $H_2O$/10% $D_2O$ at a concentration of 500 uM. HSQC spectra for FFL_001, FFL_005, FFL_006 and FFL_007 were recorded on a Bruker Avance™ 600 MHz NMR spectrometer equipped with an actively shielded z-gradient triple resonance cryoprobe. All spectra were recorded at 25° C. Spectra were processed using NMRPipe™ and NMRView™ (1,2).

Surface Plasmon Resonance

All experiments were carried out on a Biacore 2000 (GE Healthcare) at 25° C. with HBSEP (0.01 M HEPES pH 7.4, 0.15 M NaCl, 3 mM EDTA and 0.005% (v/v) Surfactant P20) (GE Healthcare) as running buffer. For binding analysis, 200-500 response units (RUs) of Motavizumab IgG were captured on a CM5 sensor chip containing 8000-9000 RUs of amine-linked mouse anti-human IgG (Human Antibody Capture kit, GE Healthcare). Samples of different protein concentrations were injected in duplicates over this surface at a flow rate of 50-100 μl/min. If necessary, surface regeneration was performed with two 60 seconds injections of 3 M $MgCl_2$ at a flow rate of 10 μl/min. One flow cell contained anti-human IgG only and its interaction with the analyte was used as reference. Alternatively, another format was used where the epitope where amine-coupled to the sensor chip and Mota Fab was injected with identical flow rates as mentioned above. Data preparation and analysis were performed using Scrubber 2.0 (BioLogic Software). For kinetic analysis, biosensor data were globally fit to a mass transport limited simple bimolecular binding model:

$$A_o \underset{k_m}{\overset{k_m}{\rightleftharpoons}} A + B \underset{k_{off}}{\overset{k_{on}}{\rightleftharpoons}} AB$$

where $A_0$ represents injected analyte.

Results for Example 1

Figure 2:
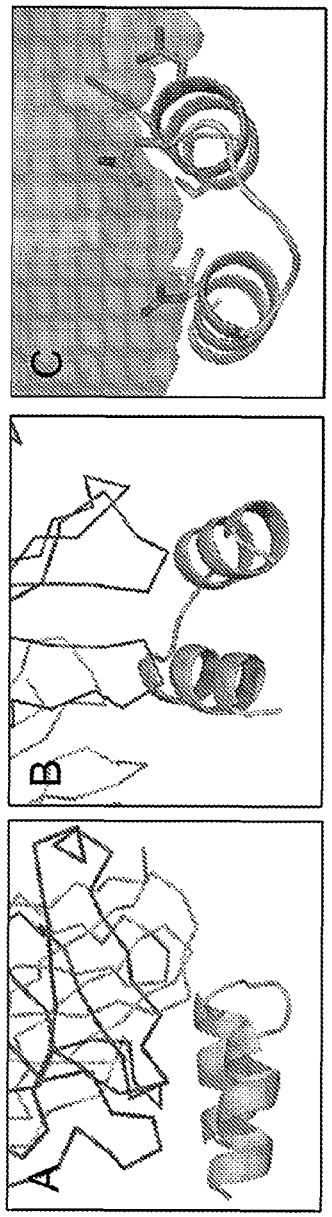
FIG. 2 shows Motavizumab (Mota) in complex with its peptide epitope from the RSVF protein. A) Side-view of the complex. B) Back-view of the complex. C) Side chains on the interface of the complex are shown in sticks.

The structure of the RSV F site A peptide bound to Motavizumab was used as the target binding site for scaffolding. (FIG. 2) This peptide structure (chain P in PDBID: 3IXT) is a helix-turn-helix motif and that led us to choose a three-helix bundle as the target topology for these scaffolds. The structure of PDBID: 3LHP, chain S was selected as the particular three-helix bundle. Procedural details of the FFL designs are shown in Table 1. The different parameters and filtering criteria used on the FFL simulations are summarized. The manual intervention stage is also summarized relative to: number of core mutations performed, the initial Rosetta energy of the designs and the Rosetta energy after the mutations and the full-atom refinement step.

TABLE 1

| | Computational | | Filtering | | Manual Intervention | |
| | | | Energy + | | | |
| | Algorithm | | Composite | Helix | Rosetta | | Rosetta energy |
| Design | SD (Å)[a] | BS design[b] | Filters | Bend[c] | energy | Mutations | (post-relax)[d] |
|---|---|---|---|---|---|---|---|
| FFL_001 | 1.5 | X | ✓ | X | — | — | — |
| FFL_002 | 3.0 | ✓ | ✓ | X | −289 | 10 | −276 |
| FFL_003 | 3.0 | ✓ | ✓ | X | −286 | 4 | −293 |
| FFL_004 | 3.0 | ✓ | ✓ | X | −285 | 7 | −291 |
| FFL_005 | 1.5 | ✓ | X | ✓ | −292 | 11 | −287 |
| FFL_006 | 3.0 | ✓ | ✓ | X | −291 | 3 | −290 |
| FFL_007 | 1.5 | ✓ | X | ✓ | −293 | 11 | −285 |
| FFL_008 | 1.5 | ✓ | X | ✓ | −293 | 8 | −286 |

[a]SD—standard deviation allowed to the constraints derived from target topology
[b]BS—Binding site design of the positions that are not in direct contact with the antibody
[c]Filtering criteria based on the helix bend angle as implemented in Helanal
[d]Rosetta energy after the mutations have been performed and a step of full atom optimization Seven scaffolds were designed using the Fold From Loops method (Table 2), and their sequences are shown in FIG. 3 along with the sequence of "T93", the template three-helix bundle from 3LHP.

TABLE 2

Protein scaffolds for the RSV F protein site A epitope

| Protein Scaffold | Reference No. |
|---|---|
| RSVF_siteA_001 | FFL 001 (SEQ ID NO: 4) |
| RSVF_siteA_002 | FFL 002 (SEQ ID NO: 5) |
| RSVF_siteA_003 | FFL 003 (SEQ ID NO: 10) |
| RSVF_siteA_004 | FFL 004 (SEQ ID NO: 6) |
| RSVF_siteA_005 | FFL 005 (SEQ ID NO: 7) |
| RSVF_siteA_006 | FFL 006 (SEQ ID NO: 8) |
| RSVF_siteA_007 | FFL 007 (SEQ ID NO: 9) |
| RSVF_siteA_008 | FFL 008 (SEQ ID NO: 12) |

The designed sequences differ from each other between 8 and 42 mutations. The structural diversity of the computational models varies from each other between 0.53 Å and 3.06 Å.

Figure 4:
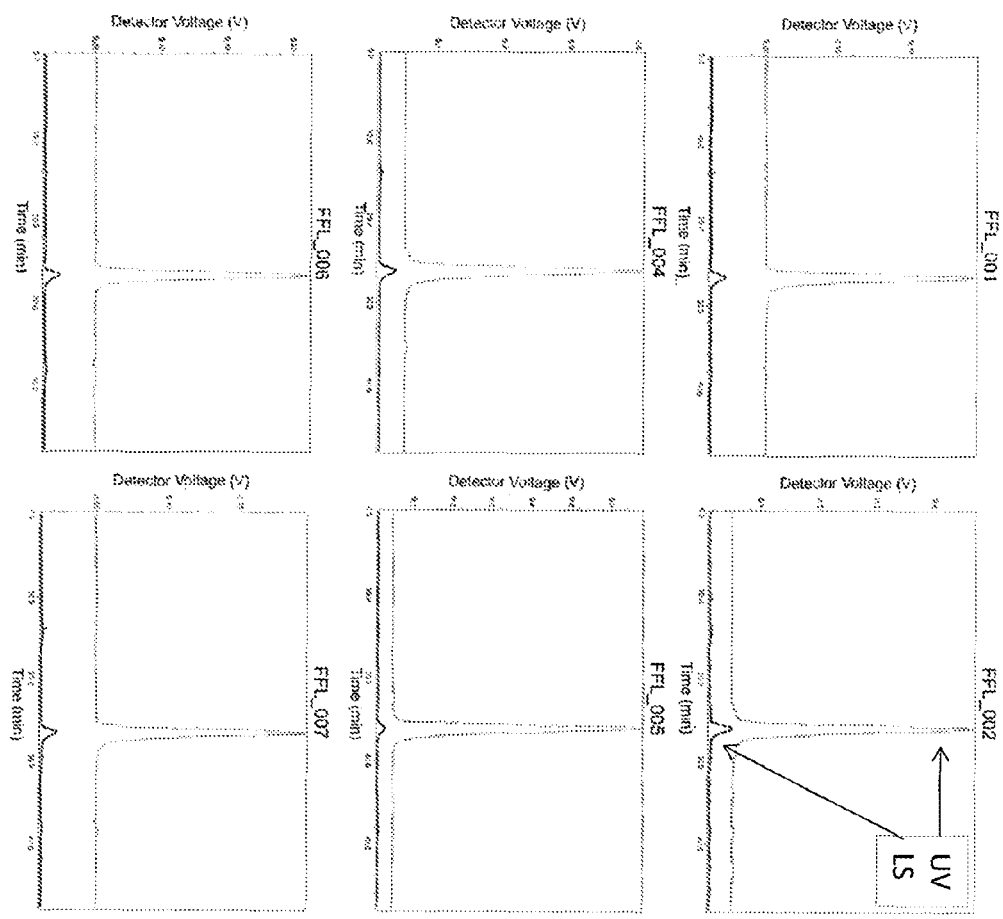
FIG. 4 shows characterization of the oligmeric state of the scaffolds by size exclusion chromatography and static light scattering. All the molecules showed a single monodisperse species and had a molecular weight close to the expected for a monomeric species, approximately 15 kDa. The UV signal from size exclusion is the upper trace in all the graphs, and the light scattering signal is the lower trace.
Figure 5:
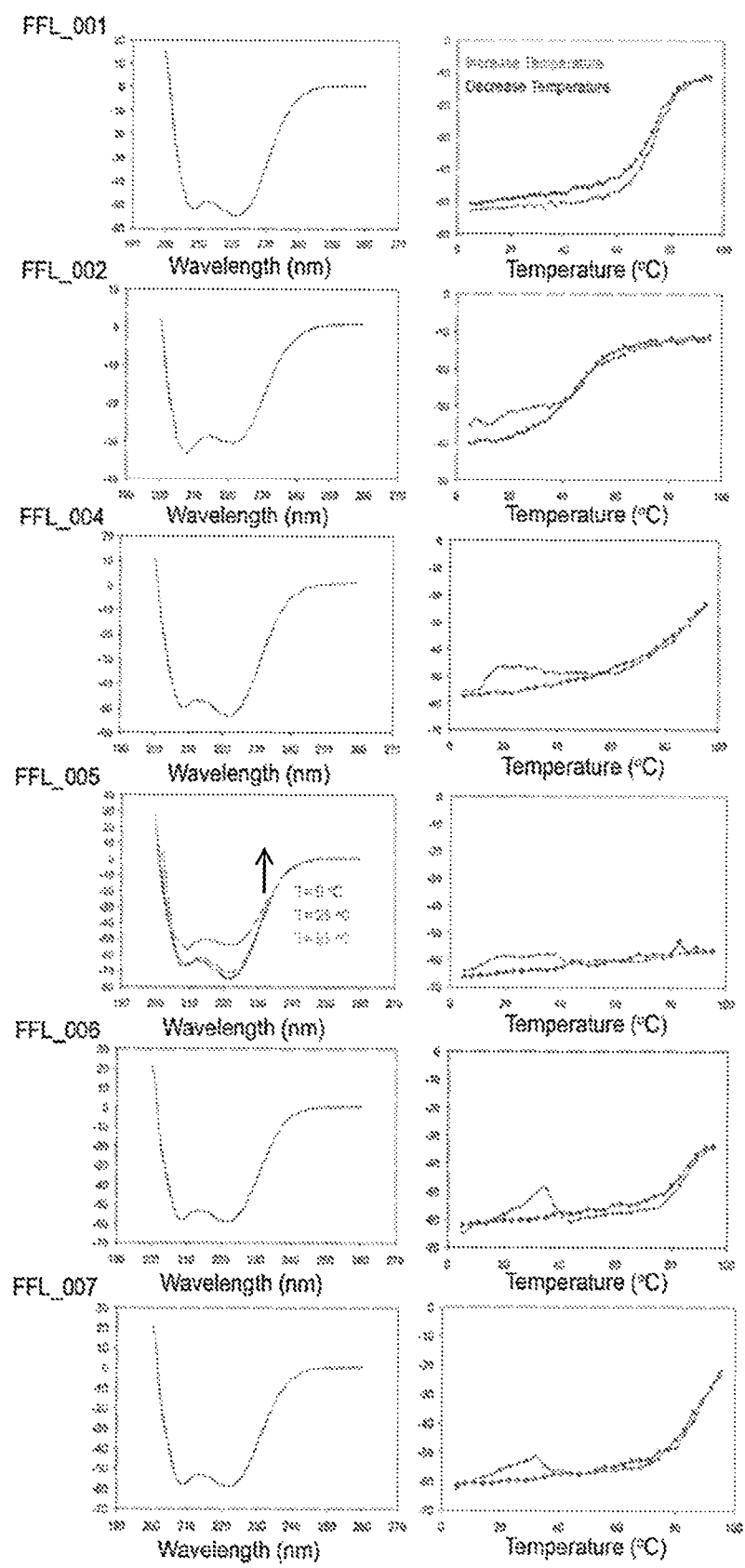
FIG. 5 shows circular dichroism analysis of secondary structure and thermal stability of FFL designs. Wavelength scans (left row) for the designs show the double minima typical for helical proteins. Thermal denaturation curves (right row) indicate cooperative unfolding for most designs, and show that FFL_005 does not melt up to 95° C. The high stability of FFL_005 is exemplified by the wavelength scan at 95° C. (left row). Melting temperatures are given in Table 1.
Figure 6:
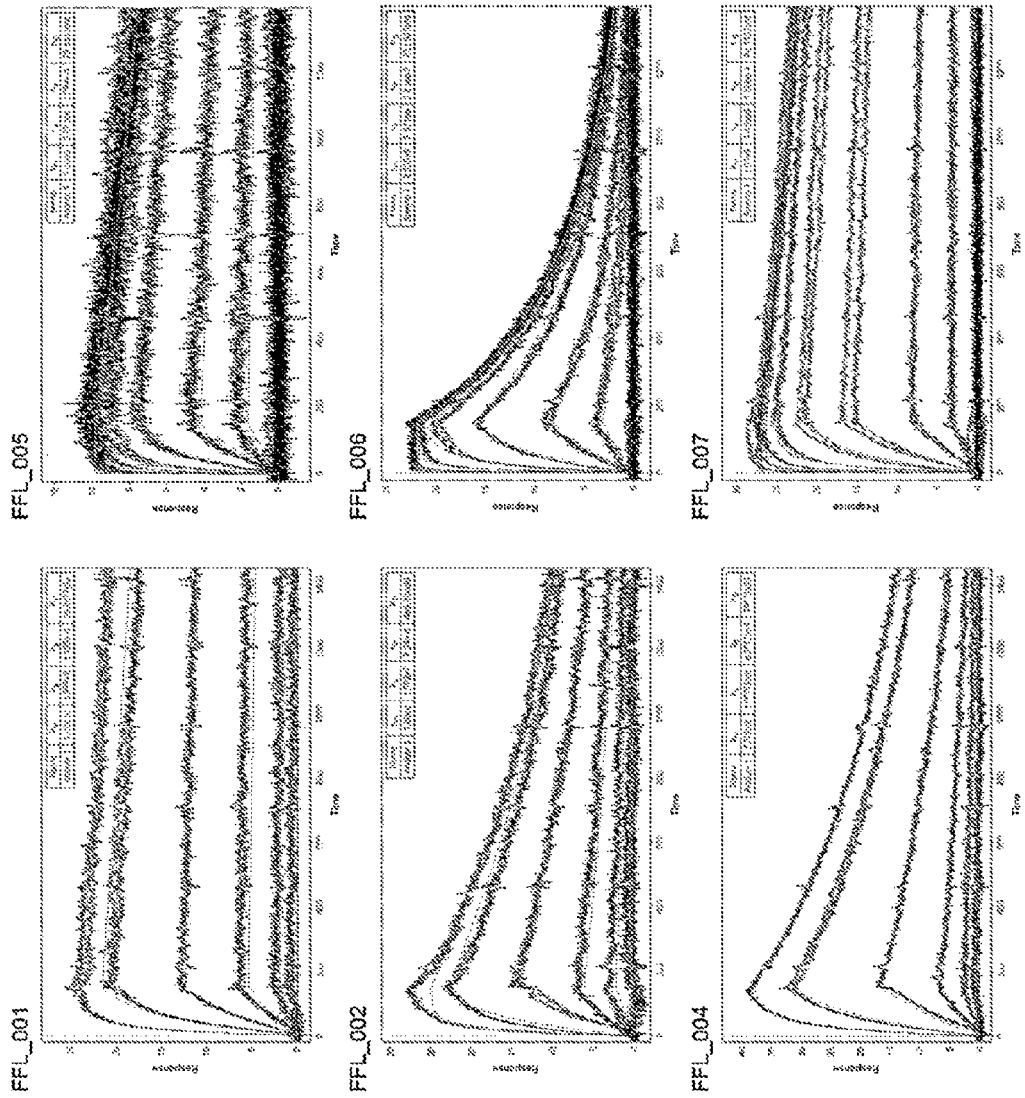
FIG. 6 shows binding of the scaffolds to Motavizumab assessed by SPR. The scaffolds were coupled to the biacore chip and Motavizumab was used as analyte. Both data and kinetic fits are shown. Kinetic fit parameters are given in Table 1.
Figure 7:
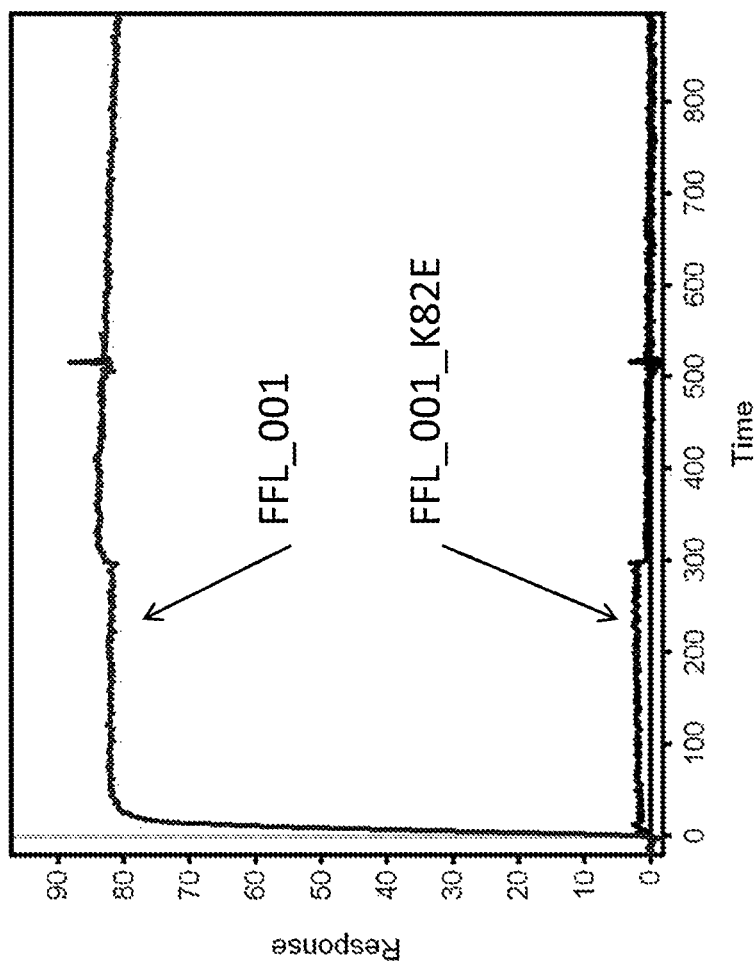
FIG. 7 shows Mota binding specificity of FFL_001 assessed by SPR. Mota IgG was the ligand, captured by anti-human IgG on the sensor chip, and FFL_001 and an epitope point mutant of FFL_001 (FFL_001_K82E) were analytes at a concentration of 22 µM. The interaction between FFL_001 and Mota was eliminated by the point mutation.

To assess expression and solubility, the recombinant proteins were expressed in E. Coli, these 7 designed variants were soluble and purifiable through steps of metal affinity chromatography (Ni++) and size exclusion chromatography (SEC) and the yields of expression ranged from 3 to 5 mg L$^{-1}$. To assess the oligomerization state in solution, the seven soluble designs were analyzed by SEC and static light scatter (FIG. 4). Six designs were monodisperse and exhibit an apparent molecular weight corresponding to the monomeric protein ($\approx$15 kDa). To evaluate the folding and the thermal stability of the designed molecules we performed circular dichroism spectroscopy (CD) (FIG. 5). The six monomeric designs showed typical CD spectra of properly folded helical proteins. Temperature induced denaturation was followed by CD showing that the stability of the designs ranged from 48 to more than 100° C. (Table 3). To test whether the functional site (mota epitope) was recreated with fidelity, binding affinities were assessed by Surface Plasmon Resonance (SPR) experiments (FIG. 6). The binding constants (K$_D$) were within 30 and 652 pM. (See Table 3) The scaffolds were coupled to the biacore chip and Motavizumab was used as analyte. The binding interaction was readily blocked by a point mutation in the epitope region (K28E), previously reported to have the same effect on the RSV context, therefore showing that the binding specificity was directed to the epitope (FIG. 7).

The affinities shown by the best FFL designs represent an improvement by a factor of approximately 7000 over a previously published K$_D$ for the peptide-epitope (200 nM). Recently, a side chain grafting strategy was utilized to transplant the RSV epitope to other heterologous scaffolds (McLellan et al., J. Mol. Biol. (2011) 409, 853-866). In that work, the highest affinity design showed a K$_D$ of 60 nM to the mota antibody. Therefore the FFL designs had KDs improved by a factor of approximately 2000 over the results of McLellan et al.

To obtain an orthogonal characterization of the solution behavior and structural properties of the designed molecules, $^{15}$N-$^{1}$H hetero-nuclear single-quantum coherence (HSQC) spectra were collected. These spectra showed good peak dispersion typical of protein with well-defined globular folds (not shown). To further evaluate the accuracy of our computational design, an x-ray structure of FFL_005 was solved. The computational model and the crystal structure of FFL_005 (not shown) were in close agreement (1.7 Å rmsd over the backbone atoms), demonstrating the validity of the computational methods for designing polypeptides with a desired structural motif and three-dimensional structure. Furthermore, the conformation of the Mota epitope within the crystal structure of FFL_005 matched the conformation of the Mota-bound peptide from PDB: 3ixt with a rmsd of 0.5 Å, supporting the claim that the FFL method can stabilize the conformation of a structural motif employed as a folding nucleus.

These studies demonstrate successful creation of novel functional proteins by coupling the in silico folding process and sequence design to simultaneously optimize the functional moiety of the molecule and the thermodynamic stability. The described computational strategy is general and flexible such that the target topology is not required to be a naturally occurring protein and back of the envelope topologies can also be used for the design of functionalized proteins. Regarding the structural complexity of the functional sites, the FFL algorithm is suited to deal with discontinuous motifs composed by multiple backbone segments, which are typically required in functional sites of naturally occurring proteins. These results have broad implications for the computational design of functional proteins and the usage of existing protein structures as potential templates.

TABLE 3

Mota binding affinities and thermal stabilities of the FFL designs. The binding affinities were assessed by SPR and the thermal stabilities by CD spectroscopy

| Molecule | T$_m$ (° C.) | SPR | | |
| --- | --- | --- | --- | --- |
| | | k$_{on}$ (M$^{-1}$s$^{-1}$) | k$_{off}$ (s$^{-1}$) | k$_{off}$/k$_{on}$ (pM) |
| FFL_001 | 75 | 3.99 × 10$^6$ | 1.19 × 10$^{-4}$ | 29.98 |
| FFL_002 | 48 | 1.56 × 10$^6$ | 7.34 × 10$^{-4}$ | 469.9 |
| FFL_004 | >85 | 1.05 × 10$^6$ | 8.32 × 10$^{-4}$ | 795 |
| FFL_005 | >100 | 2.97 × 10$^6$ | 2.09 × 10$^{-4}$ | 70.3 |
| FFL_006 | >85 | 3.57 × 10$^6$ | 2.32 × 10$^{-4}$ | 651.9 |
| FFL_007 | >85 | 1.45 × 10$^6$ | 1.36 × 10$^{-4}$ | 94.1 |

Example 2

FFL_001 scaffolds were conjugated to the surface of HepBcAg particles to improve immune responses to the epitope. The scaffolds were conjugated via hetero-bifunctional cross-linkers between an engineered cysteine in the scaffold at the opposite end from the epitope, and an engineered lysine on the tip of the major immunodominant region of HepBcAg. This oriented the scaffolds in such a way that the epitope was exposed at the radial exterior of the conjugated particle.

Figure 8:
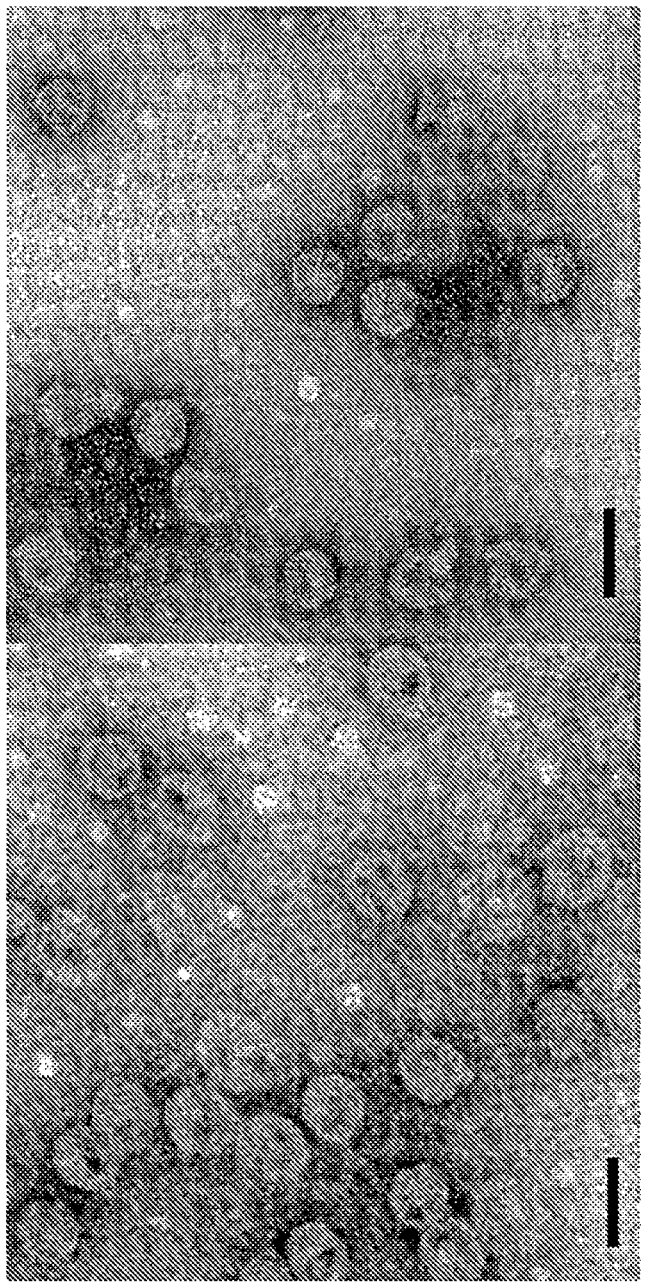
FIG. 8. Negative stain TEM of wild-type (left) and lysine-functionalized (right) HepBcAg particles. Scale bar is 50 nM.

Particles from HBcAg residues 1-149, a construct that leads to higher expression in bacteria and a predominance of the larger T=4 particle with 240 HepBcAg monomers (Zlotnick et al., 1996; Wynne et al., 1999), were expressed in E. coli and purified via standard sucrose gradients. For chemical coupling of monomeric FFL immunogens, pure lysine-functionalized HBcAg(1-149) particles were expressed and purified using standard techniques, in which a lysine residue was engineered into the tip of the immunodominant spike of every subunit. HBcAg(1-149) WT and lysine-functionalized particles were both full size (30 nm). (FIG. 8)

Conjugation of FFL_001 scaffolds and HepBcAG were carried out under standard conditions using a 10% Sucrose and 1% CHAPS, resulting in approximately 75 FFL_001 scaffolds attached to each HepB particle, according to densitometry analysis of SDS-PAGE gels run on purified fractions from sucrose gradient ultracentrifugation. Binding Mota to the FFL_001-conjugated particles was evaluated by SPR by capturing Mota IgG on the sensor chip and then binding FFL_001-particles to the Mota IgG-coated surface; subsequently Mota Fab was used as analyte and the kinetics of Mota Fab binding to Mota-IgG-captured-FFL_001-particles were evaluated; in this manner it was confirmed that the FFL_001-conjugated-particles bound to Mota with similar high affinity as FFL_001 monomers (data not shown).

Table 4 summarizes results from a macaque immunization experiment with FFL scaffold monomers and FFL_001-conjugated-HepBcAg-particles. Immunogens were scaffold monomers labeled "001", "005", and "007", and FFL_001-conjugated-HepBcAg-particles labeled "001-particle". Rhesus macaques (4 animals per immunogen) were immunized by the intramuscular route at 0, 1 and 2 months. Animals were injected with 1 mL total volume of antigen mixed with Adjuplex™ adjuvant, with 0.5 mL injected into each arm. The first immunization included a total of 200 ug of scaffold; subsequent immunizations included a total of 100 ug scaffold. "Naïve" sera was taken from each animal on day 0 before the first immunization. "Imm3" sera was taken from each animal 2 weeks after the 3$^{rd}$ immunization. Both the "Naïve" and the "Imm3" sera were evaluated for neutralization in a standard plaque reduction assay at a serum dilution of 1:20. Each sample was run in duplicate (counts for the two individual runs are shown as "Naive1", "Naive2", "Imm3_1", and "Imm3_2". The average plaque counts "Naïve_ave" and "Imm3_ave" were computed from the two runs. The % plaque reduction was calculated as (Naïve_ave−Imm3_ave)/Naïve_ave. The sera were also tested for ELISA reactivity to recombinant RSVF protein. The endpoint titers are given for each animal. The % plaque reduction numbers show a modest linear correlation with the ELISA titers, with a Pearson coefficient of 0.58.

These data demonstrate that macaque immunization with FFL scaffold monomers or FFL scaffolds presented on HepBcAg particles can result in the production of RSVF-binding antibodies and RSV neutralizing antibodies. The % neutralization (% plaque reduction) was as high as 88% for particle-displayed scaffolds, and as high as 72% for monomeric scaffolds. The average % plaque reduction for VLP-presented scaffolds was 51±25%, which was higher than the average for any of the monomer samples, the highest plaque reduction for a monomer sample being 33±11% for FFL_001 monomers. The difference in the average % plaque reduction for particle-001 compared to monomer-001 was not statistically significant. The average RSVF ELISA titer was also higher for the particle-001 sample (94000±20000) compared to the highest titer monomer sample (79000±66000 for FFL_001), but again the difference was not statistically significant.

TABLE 4

| Immunogen | NHP id | % plaque reduction | RSVF ELISA titer | Naïve_ave | Naive 1 | Naive 2 | Imm3_ave | Imm3_1 | Imm3_2 |
|---|---|---|---|---|---|---|---|---|---|
| 001-particle | D039 | 0.8757 | 120000 | 84.5 | 83 | 86 | 10.5 | 13 | 8 |
| 007 | D030 | 0.717 | 110000 | 79.5 | 80 | 79 | 22.5 | 21 | 24 |
| 005 | D180 | 0.5924 | 22000 | 78.5 | 72 | 85 | 32 | 35 | 29 |
| 001 | C012 | 0.4536 | 170000 | 91.5 | 89 | 94 | 50 | 46 | 54 |
| 001-particle | C004 | 0.4491 | 93000 | 83.5 | 74 | 93 | 46 | 50 | 42 |
| 001-particle | D130 | 0.4207 | 91000 | 72.5 | 68 | 77 | 42 | 43 | 41 |
| 007 | D227 | 0.3716 | 23000 | 91.5 | 84 | 99 | 57.5 | 57 | 58 |
| 007 | C010 | 0.3709 | 36000 | 75.5 | 70 | 81 | 47.5 | 44 | 51 |
| 001 | D027 | 0.3642 | 12000 | 75.5 | 81 | 70 | 48 | 46 | 50 |
| 001 | D052 | 0.3243 | 65000 | 92.5 | 89 | 96 | 62.5 | 63 | 62 |
| 001-particle | D184 | 0.3038 | 72000 | 79 | 72 | 86 | 55 | 52 | 58 |
| 005 | D104 | 0.2 | 8500 | 67.5 | 64 | 71 | 54 | 54 | 54 |
| 001 | D172 | 0.1954 | 69000 | 87 | 88 | 86 | 70 | 65 | 75 |
| 005 | D190 | 0.1931 | 4800 | 72.5 | 68 | 77 | 58.5 | 50 | 67 |
| 005 | D032 | 0.1243 | 9500 | 88.5 | 85 | 92 | 77.5 | 78 | 77 |
| 007 | D087 | 0.047 | 15000 | 74.5 | 73 | 76 | 71 | 70 | 72 |

We claim:

1. An isolated polypeptide comprising the amino acid sequence according to SEQ ID NO:2, wherein residue 1 is G, residue 2 is S, and residue 6 is selected from the group consisting of A, I, M, and V.

2. The isolated polypeptide of claim 1, comprising an amino acid sequence according to SEQ ID NO:3.

3. The isolated polypeptide of claim 1, wherein the polypeptide comprises a sequence selected from the group consisting of SEQ ID NOS:4-9.

4. The isolated polypeptide of claim 1, wherein the polypeptide comprises a sequence selected from the group consisting of SEQ ID NO:4, SEQ ID NO:5, SEQ ID NO:7, and SEQ ID NO:9.

5. The isolated polypeptide of claim 1, wherein the polypeptide comprises a sequence selected from the group consisting of SEQ ID NO:4, SEQ ID NO:7, and SEQ ID NO:9.

6. An isolated nucleic acid encoding the polypeptide of claim 1.

7. A recombinant expression vector comprising the isolated nucleic acid of claim 6 operatively linked to a promoter.

8. A recombinant host cell comprising the recombinant expression vector of claim 7.

9. A pharmaceutical composition, comprising the polypeptide of claim 1, and a pharmaceutically acceptable carrier.

10. A method for treating a respiratory syncytial virus (RSV) infection, comprising administering to a subject infected with RSV an amount effective to treat the infection of the polypeptide of claim 1.

11. A method for generating an immune response in a subject, comprising administering to the subject an amount effective to generate an immune response of the polypeptide of claim 1.

12. A method for treating a respiratory syncytial virus (RSV) infection, comprising administering to a subject infected with RSV an amount effective to treat the infection of the polypeptide of claim 2.

13. A method for treating a respiratory syncytial virus (RSV) infection, comprising administering to a subject infected with RSV an amount effective to treat the infection of the polypeptide of claim 3.

14. A method for treating a respiratory syncytial virus (RSV) infection, comprising administering to a subject infected with RSV an amount effective to treat the infection of the polypeptide of claim 4.

15. A method for treating a respiratory syncytial virus (RSV) infection, comprising administering to a subject infected with RSV an amount effective to treat the infection of the polypeptide of claim 5.

16. A method for generating an immune response in a subject, comprising administering to the subject an amount effective to generate an immune response of the polypeptide of claim 2.

17. A method for generating an immune response in a subject, comprising administering to the subject an amount effective to generate an immune response of the polypeptide of claim 3.

18. A method for generating an immune response in a subject, comprising administering to the subject an amount effective to generate an immune response of the polypeptide of claim 4.

19. A method for generating an immune response in a subject, comprising administering to the subject an amount effective to generate an immune response of the polypeptide of claim 5.

* * * * *

SEQUENCE LISTING

<160> NUMBER OF SEQ ID NOS: 12

<210> SEQ ID NO 1
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is G or optionally absent
<220> FEATURE:
<221> NAME/KEY: MISC_FEATURE
<222> LOCATION: (2)..(2)
<223> OTHER INFORMATION: X is S or optionally absent
<220> FEATURE:
<221> NAME/KEY: MISC_FEATURE
<222> LOCATION: (3)..(3)
<223> OTHER INFORMATION: X is M, L, R, or F
<220> FEATURE:
<221> NAME/KEY: MISC_FEATURE
<222> LOCATION: (6)..(6)
<223> OTHER INFORMATION: X is R, A, I, M, V, or L
<220> FEATURE:
<221> NAME/KEY: MISC_FEATURE
<222> LOCATION: (7)..(7)
<223> OTHER INFORMATION: X is R or M
<220> FEATURE:
<221> NAME/KEY: MISC_FEATURE
<222> LOCATION: (10)..(10)
<223> OTHER INFORMATION: X is L, A, or V
<220> FEATURE:
<221> NAME/KEY: MISC_FEATURE

```
<222> LOCATION: (12)..(12)
<223> OTHER INFORMATION: X is E, R, K, or D
<220> FEATURE:
<221> NAME/KEY: MISC_FEATURE
<222> LOCATION: (14)..(14)
<223> OTHER INFORMATION: X is L, F, I, or A
<220> FEATURE:
<221> NAME/KEY: MISC_FEATURE
<222> LOCATION: (17)..(17)
<223> OTHER INFORMATION: X is L, F, or A
<220> FEATURE:
<221> NAME/KEY: MISC_FEATURE
<222> LOCATION: (18)..(18)
<223> OTHER INFORMATION: X is L, V, F, or M
<220> FEATURE:
<221> NAME/KEY: MISC_FEATURE
<222> LOCATION: (21)..(21)
<223> OTHER INFORMATION: X is A, V, F, I or L
<220> FEATURE:
<221> NAME/KEY: MISC_FEATURE
<222> LOCATION: (25)..(25)
<223> OTHER INFORMATION: X is E, M, L, F, W, or V
<220> FEATURE:
<221> NAME/KEY: MISC_FEATURE
<222> LOCATION: (28)..(28)
<223> OTHER INFORMATION: X is E, M, L, F, I, or V
<220> FEATURE:
<221> NAME/KEY: MISC_FEATURE
<222> LOCATION: (32)..(32)
<223> OTHER INFORMATION: X is M, L, F, or I
<220> FEATURE:
<221> NAME/KEY: MISC_FEATURE
<222> LOCATION: (35)..(35)
<223> OTHER INFORMATION: X is R, E, G, D, or Q
<220> FEATURE:
<221> NAME/KEY: MISC_FEATURE
<222> LOCATION: (36)..(36)
<223> OTHER INFORMATION: X is G, D, P, W, E, or Q
<220> FEATURE:
<221> NAME/KEY: MISC_FEATURE
<222> LOCATION: (37)..(37)
<223> OTHER INFORMATION: X is Q, I, P, K or F
<220> FEATURE:
<221> NAME/KEY: MISC_FEATURE
<222> LOCATION: (38)..(38)
<223> OTHER INFORMATION: X is R, Q, K, S, G, or H
<220> FEATURE:
<221> NAME/KEY: MISC_FEATURE
<222> LOCATION: (42)..(42)
<223> OTHER INFORMATION: X is M, K, R, or A
<220> FEATURE:
<221> NAME/KEY: MISC_FEATURE
<222> LOCATION: (45)..(45)
<223> OTHER INFORMATION: X is W, L, M or K
<220> FEATURE:
<221> NAME/KEY: MISC_FEATURE
<222> LOCATION: (46)..(46)
<223> OTHER INFORMATION: X is A, M, K, or F
<220> FEATURE:
<221> NAME/KEY: MISC_FEATURE
<222> LOCATION: (48)..(48)
<223> OTHER INFORMATION: X is I, F, L, E, K, or D
<220> FEATURE:
<221> NAME/KEY: MISC_FEATURE
<222> LOCATION: (49)..(49)
<223> OTHER INFORMATION: X is A, V, M, F, or L
<220> FEATURE:
<221> NAME/KEY: MISC_FEATURE
<222> LOCATION: (51)..(51)
<223> OTHER INFORMATION: X is D, K, E, or Y
<220> FEATURE:
<221> NAME/KEY: MISC_FEATURE
<222> LOCATION: (53)..(53)
<223> OTHER INFORMATION: X is F, V, A, R, M, or L
<220> FEATURE:
<221> NAME/KEY: MISC_FEATURE
<222> LOCATION: (56)..(56)
<223> OTHER INFORMATION: X is F, L, A, V, or M
<220> FEATURE:
```

```
<221> NAME/KEY: MISC_FEATURE
<222> LOCATION: (58)..(58)
<223> OTHER INFORMATION: X is K or R
<220> FEATURE:
<221> NAME/KEY: MISC_FEATURE
<222> LOCATION: (60)..(60)
<223> OTHER INFORMATION: X is V, M, or I
<220> FEATURE:
<221> NAME/KEY: MISC_FEATURE
<222> LOCATION: (63)..(63)
<223> OTHER INFORMATION: X is F, R, V, I, A, or Y
<220> FEATURE:
<221> NAME/KEY: MISC_FEATURE
<222> LOCATION: (64)..(64)
<223> OTHER INFORMATION: X is L, E, or A
<220> FEATURE:
<221> NAME/KEY: MISC_FEATURE
<222> LOCATION: (65)..(65)
<223> OTHER INFORMATION: X is S or optionally absent
<220> FEATURE:
<221> NAME/KEY: MISC_FEATURE
<222> LOCATION: (66)..(66)
<223> OTHER INFORMATION: X is E or optionally absent
<220> FEATURE:
<221> NAME/KEY: MISC_FEATURE
<222> LOCATION: (67)..(67)
<223> OTHER INFORMATION: X is A or L
<220> FEATURE:
<221> NAME/KEY: MISC_FEATURE
<222> LOCATION: (68)..(68)
<223> OTHER INFORMATION: X is L or optionally absent
<220> FEATURE:
<221> NAME/KEY: MISC_FEATURE
<222> LOCATION: (69)..(69)
<223> OTHER INFORMATION: X is S or optionally absent
<220> FEATURE:
<221> NAME/KEY: MISC_FEATURE
<222> LOCATION: (71)..(71)
<223> OTHER INFORMATION: X is I or optionally absent
<220> FEATURE:
<221> NAME/KEY: MISC_FEATURE
<222> LOCATION: (72)..(72)
<223> OTHER INFORMATION: X is N or optionally absent
<220> FEATURE:
<221> NAME/KEY: MISC_FEATURE
<222> LOCATION: (74)..(74)
<223> OTHER INFORMATION: X is Y, M or L
<220> FEATURE:
<221> NAME/KEY: MISC_FEATURE
<222> LOCATION: (75)..(75)
<223> OTHER INFORMATION: X is P or optionally absent
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: MISC_FEATURE
<222> LOCATION: (78)..(78)
<223> OTHER INFORMATION: X is N or optionally absent
<220> FEATURE:
<221> NAME/KEY: MISC_FEATURE
<222> LOCATION: (79)..(79)
<223> OTHER INFORMATION: X is D or optionally absent
<220> FEATURE:
<221> NAME/KEY: MISC_FEATURE
<222> LOCATION: (80)..(80)
<223> OTHER INFORMATION: X is D, Q or K
<220> FEATURE:
<221> NAME/KEY: MISC_FEATURE
<222> LOCATION: (81)..(82)
<223> OTHER INFORMATION: X is K or optionally absent
<220> FEATURE:
<221> NAME/KEY: MISC_FEATURE
<222> LOCATION: (83)..(83)
<223> OTHER INFORMATION: X is L or optionally absent
<220> FEATURE:
<221> NAME/KEY: MISC_FEATURE
<222> LOCATION: (84)..(84)
<223> OTHER INFORMATION: X is T, I, M, V, or A
```

-continued

```
<220> FEATURE:
<221> NAME/KEY: MISC_FEATURE
<222> LOCATION: (85)..(85)
<223> OTHER INFORMATION: X is S or optionally absent
<220> FEATURE:
<221> NAME/KEY: MISC_FEATURE
<222> LOCATION: (86)..(86)
<223> OTHER INFORMATION: X is N or optionally absent
<220> FEATURE:
<221> NAME/KEY: MISC_FEATURE
<222> LOCATION: (87)..(87)
<223> OTHER INFORMATION: X is D or K
<220> FEATURE:
<221> NAME/KEY: MISC_FEATURE
<222> LOCATION: (88)..(88)
<223> OTHER INFORMATION: X is A, T, L, V, or I
<220> FEATURE:
<221> NAME/KEY: MISC_FEATURE
<222> LOCATION: (89)..(89)
<223> OTHER INFORMATION: X is K, L  or I
<220> FEATURE:
<221> NAME/KEY: MISC_FEATURE
<222> LOCATION: (91)..(91)
<223> OTHER INFORMATION: X is F, Y, K, E, R, or L
<220> FEATURE:
<221> NAME/KEY: MISC_FEATURE
<222> LOCATION: (92)..(92)
<223> OTHER INFORMATION: X is D, A, V, or M
<220> FEATURE:
<221> NAME/KEY: MISC_FEATURE
<222> LOCATION: (93)..(93)
<223> OTHER INFORMATION: X is  A or optionally absent
<220> FEATURE:
<221> NAME/KEY: MISC_FEATURE
<222> LOCATION: (94)..(94)
<223> OTHER INFORMATION: X is E, I, or R
<220> FEATURE:
<221> NAME/KEY: MISC_FEATURE
<222> LOCATION: (95)..(95)
<223> OTHER INFORMATION: X is V, A, M or L
<220> FEATURE:
<221> NAME/KEY: MISC_FEATURE
<222> LOCATION: (96)..(96)
<223> OTHER INFORMATION: X is A, E, K, F, M, or W
<220> FEATURE:
<221> NAME/KEY: MISC_FEATURE
<222> LOCATION: (99)..(99)
<223> OTHER INFORMATION: X is L, I, or V
<220> FEATURE:
<221> NAME/KEY: MISC_FEATURE
<222> LOCATION: (101)..(101)
<223> OTHER INFORMATION: X is A or L
<220> FEATURE:
<221> NAME/KEY: MISC_FEATURE
<222> LOCATION: (102)..(102)
<223> OTHER INFORMATION: X is F, M, L, E, or I
<220> FEATURE:
<221> NAME/KEY: MISC_FEATURE
<222> LOCATION: (103)..(103)
<223> OTHER INFORMATION: X is K, A, V, M, I or L
<220> FEATURE:
<221> NAME/KEY: MISC_FEATURE
<222> LOCATION: (106)..(106)
<223> OTHER INFORMATION: X is A, V, or I
<220> FEATURE:
<221> NAME/KEY: MISC_FEATURE
<222> LOCATION: (108)..(108)
<223> OTHER INFORMATION: X is E, R, D, K, I, or A
<220> FEATURE:
<221> NAME/KEY: MISC_FEATURE
<222> LOCATION: (109)..(109)
<223> OTHER INFORMATION: X is A, M, K, L, or W
<220> FEATURE:
<221> NAME/KEY: MISC_FEATURE
<222> LOCATION: (110)..(110)
<223> OTHER INFORMATION: X is A, F, V or K
<220> FEATURE:
<221> NAME/KEY: MISC_FEATURE
<222> LOCATION: (113)..(113)
```

```
<223> OTHER INFORMATION: X is G or optionally absent
<220> FEATURE:
<221> NAME/KEY: MISC_FEATURE
<222> LOCATION: (114)..(114)
<223> OTHER INFORMATION: X is S or optionally absent
<220> FEATURE:
<221> NAME/KEY: MISC_FEATURE
<222> LOCATION: (115)..(115)
<223> OTHER INFORMATION: X is W or optionally absent

<400> SEQUENCE: 1

Xaa Xaa Xaa Ser Asp Xaa Xaa Lys Asp Xaa Glu Xaa Arg Xaa Asp Lys
 1               5                  10                  15

Xaa Xaa Glu Ala Xaa Lys Asn Lys Xaa Asp Lys Xaa Lys Ala Ala Xaa
            20                  25                  30

Arg Lys Xaa Xaa Xaa Xaa Glu Glu Arg Xaa Lys Asp Xaa Xaa Lys Xaa
        35                  40                  45

Xaa Arg Xaa Glu Xaa Glu Gln Xaa Arg Xaa Ala Xaa Arg Asn Xaa Xaa
        50                  55                  60

Xaa Xaa Xaa Xaa Xaa Lys Xaa Xaa Asp Xaa Xaa Ile Xaa Xaa Xaa Xaa
65                  70                  75                  80

Xaa Xaa Xaa Xaa Xaa Xaa Xaa Xaa Xaa Lys Xaa Xaa Xaa Xaa Xaa Xaa
                85                  90                  95

Lys Lys Xaa Glu Xaa Xaa Xaa Ala Asp Xaa Glu Xaa Xaa Xaa Thr Gln
            100                 105                 110

Xaa Xaa Xaa
       115

<210> SEQ ID NO 2
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is G or optionally absent
<220> FEATURE:
<221> NAME/KEY: MISC_FEATURE
<222> LOCATION: (2)..(2)
<223> OTHER INFORMATION: X is S or optionally absent
<220> FEATURE:
<221> NAME/KEY: MISC_FEATURE
<222> LOCATION: (3)..(3)
<223> OTHER INFORMATION: X is M, L, R or F
<220> FEATURE:
<221> NAME/KEY: MISC_FEATURE
<222> LOCATION: (6)..(6)
<223> OTHER INFORMATION: X is R, A, I, M or V
<220> FEATURE:
<221> NAME/KEY: MISC_FEATURE
<222> LOCATION: (10)..(10)
<223> OTHER INFORMATION: X is L, A or V
<220> FEATURE:
<221> NAME/KEY: MISC_FEATURE
<222> LOCATION: (12)..(12)
<223> OTHER INFORMATION: X is E, R, K or D
<220> FEATURE:
<221> NAME/KEY: MISC_FEATURE
<222> LOCATION: (14)..(14)
<223> OTHER INFORMATION: X is L, F, I or A
<220> FEATURE:
<221> NAME/KEY: MISC_FEATURE
<222> LOCATION: (17)..(17)
<223> OTHER INFORMATION: X is L, F, or A
<220> FEATURE:
<221> NAME/KEY: MISC_FEATURE
<222> LOCATION: (18)..(18)
<223> OTHER INFORMATION: X is L, V, or F
```

```
<220> FEATURE:
<221> NAME/KEY: MISC_FEATURE
<222> LOCATION: (21)..(21)
<223> OTHER INFORMATION: X is A, V, F, or L
<220> FEATURE:
<221> NAME/KEY: MISC_FEATURE
<222> LOCATION: (25)..(25)
<223> OTHER INFORMATION: X is M, L, F or V
<220> FEATURE:
<221> NAME/KEY: MISC_FEATURE
<222> LOCATION: (28)..(28)
<223> OTHER INFORMATION: X is F, M, E or I
<220> FEATURE:
<221> NAME/KEY: MISC_FEATURE
<222> LOCATION: (32)..(32)
<223> OTHER INFORMATION: X is M, L, F, or I
<220> FEATURE:
<221> NAME/KEY: MISC_FEATURE
<222> LOCATION: (35)..(35)
<223> OTHER INFORMATION: X is R, E, G or D
<220> FEATURE:
<221> NAME/KEY: MISC_FEATURE
<222> LOCATION: (36)..(36)
<223> OTHER INFORMATION: X is G, D, P, W, or Q
<220> FEATURE:
<221> NAME/KEY: MISC_FEATURE
<222> LOCATION: (37)..(37)
<223> OTHER INFORMATION: X is Q, I, P or F
<220> FEATURE:
<221> NAME/KEY: MISC_FEATURE
<222> LOCATION: (38)..(38)
<223> OTHER INFORMATION: X is R, Q, K, S or H
<220> FEATURE:
<221> NAME/KEY: MISC_FEATURE
<222> LOCATION: (42)..(42)
<223> OTHER INFORMATION: X is M, K, R, or A
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: MISC_FEATURE
<222> LOCATION: (46)..(46)
<223> OTHER INFORMATION: X is A, M, F or K
<220> FEATURE:
<221> NAME/KEY: MISC_FEATURE
<222> LOCATION: (48)..(48)
<223> OTHER INFORMATION: X is I, F, L, E, K or D
<220> FEATURE:
<221> NAME/KEY: MISC_FEATURE
<222> LOCATION: (49)..(49)
<223> OTHER INFORMATION: X is A, V, M, F or L
<220> FEATURE:
<221> NAME/KEY: MISC_FEATURE
<222> LOCATION: (51)..(51)
<223> OTHER INFORMATION: X is D, K, Y or E
<220> FEATURE:
<221> NAME/KEY: MISC_FEATURE
<222> LOCATION: (53)..(53)
<223> OTHER INFORMATION: X is F, V, A, R or M
<220> FEATURE:
<221> NAME/KEY: MISC_FEATURE
<222> LOCATION: (56)..(56)
<223> OTHER INFORMATION: X is F, L, A, V or M
<220> FEATURE:
<221> NAME/KEY: MISC_FEATURE
<222> LOCATION: (58)..(58)
<223> OTHER INFORMATION: X is K or R
<220> FEATURE:
<221> NAME/KEY: MISC_FEATURE
<222> LOCATION: (60)..(60)
<223> OTHER INFORMATION: X is V, M or I
<220> FEATURE:
<221> NAME/KEY: MISC_FEATURE
<222> LOCATION: (63)..(63)
<223> OTHER INFORMATION: X is F, R, V, I or Y
<220> FEATURE:
<221> NAME/KEY: MISC_FEATURE
<222> LOCATION: (64)..(64)
```

```
<223> OTHER INFORMATION: X is L, E or A
<220> FEATURE:
<221> NAME/KEY: MISC_FEATURE
<222> LOCATION: (67)..(67)
<223> OTHER INFORMATION: X is A or L
<220> FEATURE:
<221> NAME/KEY: MISC_FEATURE
<222> LOCATION: (74)..(74)
<223> OTHER INFORMATION: X is Y, M or L
<220> FEATURE:
<221> NAME/KEY: MISC_FEATURE
<222> LOCATION: (80)..(80)
<223> OTHER INFORMATION: X is D, Q or K
<220> FEATURE:
<221> NAME/KEY: MISC_FEATURE
<222> LOCATION: (84)..(84)
<223> OTHER INFORMATION: X is T, I, M, V or A
<220> FEATURE:
<221> NAME/KEY: MISC_FEATURE
<222> LOCATION: (88)..(88)
<223> OTHER INFORMATION: X is T, L, V  or I
<220> FEATURE:
<221> NAME/KEY: MISC_FEATURE
<222> LOCATION: (89)..(89)
<223> OTHER INFORMATION: X is K, L or I
<220> FEATURE:
<221> NAME/KEY: MISC_FEATURE
<222> LOCATION: (91)..(91)
<223> OTHER INFORMATION: X is F, Y, K, E or L
<220> FEATURE:
<221> NAME/KEY: MISC_FEATURE
<222> LOCATION: (92)..(92)
<223> OTHER INFORMATION: X is D, A, V or M
<220> FEATURE:
<221> NAME/KEY: MISC_FEATURE
<222> LOCATION: (94)..(94)
<223> OTHER INFORMATION: X is E, I, or R
<220> FEATURE:
<221> NAME/KEY: MISC_FEATURE
<222> LOCATION: (95)..(95)
<223> OTHER INFORMATION: X is V, A, M or L
<220> FEATURE:
<221> NAME/KEY: MISC_FEATURE
<222> LOCATION: (96)..(96)
<223> OTHER INFORMATION: X is E, K, F or W
<220> FEATURE:
<221> NAME/KEY: MISC_FEATURE
<222> LOCATION: (99)..(99)
<223> OTHER INFORMATION: X is L, I or V
<220> FEATURE:
<221> NAME/KEY: MISC_FEATURE
<222> LOCATION: (101)..(101)
<223> OTHER INFORMATION: X is A or L
<220> FEATURE:
<221> NAME/KEY: MISC_FEATURE
<222> LOCATION: (102)..(102)
<223> OTHER INFORMATION: X is F, M, L, E or I
<220> FEATURE:
<221> NAME/KEY: MISC_FEATURE
<222> LOCATION: (103)..(103)
<223> OTHER INFORMATION: X is K, A, V, M or L
<220> FEATURE:
<221> NAME/KEY: MISC_FEATURE
<222> LOCATION: (106)..(106)
<223> OTHER INFORMATION: X is A, V or I
<220> FEATURE:
<221> NAME/KEY: MISC_FEATURE
<222> LOCATION: (108)..(108)
<223> OTHER INFORMATION: X is E, R, D, K, A or I
<220> FEATURE:
<221> NAME/KEY: MISC_FEATURE
<222> LOCATION: (109)..(109)
<223> OTHER INFORMATION: X is A, M, K, L or W
<220> FEATURE:
<221> NAME/KEY: MISC_FEATURE
<222> LOCATION: (110)..(110)
<223> OTHER INFORMATION: X is A, F or V
<220> FEATURE:
<221> NAME/KEY: MISC_FEATURE
```

```
<222> LOCATION: (113)..(113)
<223> OTHER INFORMATION: X is G or optionally absent
<220> FEATURE:
<221> NAME/KEY: MISC_FEATURE
<222> LOCATION: (114)..(114)
<223> OTHER INFORMATION: X is S or optionally absent
<220> FEATURE:
<221> NAME/KEY: MISC_FEATURE
<222> LOCATION: (115)..(115)
<223> OTHER INFORMATION: X is W or optionally absent

<400> SEQUENCE: 2

Xaa Xaa Xaa Ser Asp Xaa Arg Lys Asp Xaa Glu Xaa Arg Xaa Asp Lys
1               5                   10                  15

Xaa Xaa Glu Ala Xaa Lys Asn Lys Xaa Asp Lys Xaa Lys Ala Ala Xaa
            20                  25                  30

Arg Lys Xaa Xaa Xaa Xaa Glu Glu Arg Xaa Lys Asp Xaa Xaa Lys Xaa
        35                  40                  45

Xaa Arg Xaa Glu Xaa Glu Gln Xaa Arg Xaa Ala Xaa Arg Asn Xaa Xaa
    50                  55                  60

Ser Glu Xaa Leu Ser Lys Ile Asn Asp Xaa Pro Ile Thr Asn Asp Xaa
65              70                  75                  80

Lys Lys Leu Xaa Ser Asn Asp Xaa Xaa Lys Xaa Xaa Ala Xaa Xaa Xaa
                85                  90                  95

Lys Lys Xaa Glu Xaa Xaa Xaa Ala Asp Xaa Glu Xaa Xaa Xaa Thr Gln
            100                 105                 110

Xaa Xaa Xaa
        115

<210> SEQ ID NO 3
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is G or optionally absent
<220> FEATURE:
<221> NAME/KEY: MISC_FEATURE
<222> LOCATION: (2)..(2)
<223> OTHER INFORMATION: X is S or optionally absent
<220> FEATURE:
<221> NAME/KEY: MISC_FEATURE
<222> LOCATION: (3)..(3)
<223> OTHER INFORMATION: X is M, L, R or F
<220> FEATURE:
<221> NAME/KEY: MISC_FEATURE
<222> LOCATION: (6)..(6)
<223> OTHER INFORMATION: X is I or M
<220> FEATURE:
<221> NAME/KEY: MISC_FEATURE
<222> LOCATION: (10)..(10)
<223> OTHER INFORMATION: X is L or A
<220> FEATURE:
<221> NAME/KEY: MISC_FEATURE
<222> LOCATION: (12)..(12)
<223> OTHER INFORMATION: X is E, R or D
<220> FEATURE:
<221> NAME/KEY: MISC_FEATURE
<222> LOCATION: (14)..(14)
<223> OTHER INFORMATION: X is F or A
<220> FEATURE:
<221> NAME/KEY: MISC_FEATURE
<222> LOCATION: (17)..(17)
<223> OTHER INFORMATION: X is L, F or A
<220> FEATURE:
<221> NAME/KEY: MISC_FEATURE
<222> LOCATION: (18)..(18)
```

```
<223> OTHER INFORMATION: X is F or V
<220> FEATURE:
<221> NAME/KEY: MISC_FEATURE
<222> LOCATION: (21)..(21)
<223> OTHER INFORMATION: X is A, V or L
<220> FEATURE:
<221> NAME/KEY: MISC_FEATURE
<222> LOCATION: (25)..(25)
<223> OTHER INFORMATION: X is L, F or W
<220> FEATURE:
<221> NAME/KEY: MISC_FEATURE
<222> LOCATION: (28)..(28)
<223> OTHER INFORMATION: X is F, M or I
<220> FEATURE:
<221> NAME/KEY: MISC_FEATURE
<222> LOCATION: (32)..(32)
<223> OTHER INFORMATION: X is L, F or I
<220> FEATURE:
<221> NAME/KEY: MISC_FEATURE
<222> LOCATION: (35)..(35)
<223> OTHER INFORMATION: X is E, G or D
<220> FEATURE:
<221> NAME/KEY: MISC_FEATURE
<222> LOCATION: (36)..(36)
<223> OTHER INFORMATION: X is G, D, W or Q
<220> FEATURE:
<221> NAME/KEY: MISC_FEATURE
<222> LOCATION: (37)..(37)
<223> OTHER INFORMATION: X is Q, I, P or F
<220> FEATURE:
<221> NAME/KEY: MISC_FEATURE
<222> LOCATION: (38)..(38)
<223> OTHER INFORMATION: X is Q, K, S or H
<220> FEATURE:
<221> NAME/KEY: MISC_FEATURE
<222> LOCATION: (42)..(42)
<223> OTHER INFORMATION: X is M, R, or A
<220> FEATURE:
<221> NAME/KEY: MISC_FEATURE
<222> LOCATION: (45)..(45)
<223> OTHER INFORMATION: X is W, L or M
<220> FEATURE:
<221> NAME/KEY: MISC_FEATURE
<222> LOCATION: (46)..(46)
<223> OTHER INFORMATION: X is M, K or F
<220> FEATURE:
<221> NAME/KEY: MISC_FEATURE
<222> LOCATION: (48)..(48)
<223> OTHER INFORMATION: X is F, L, K or D
<220> FEATURE:
<221> NAME/KEY: MISC_FEATURE
<222> LOCATION: (49)..(49)
<223> OTHER INFORMATION: X is A, M or L
<220> FEATURE:
<221> NAME/KEY: MISC_FEATURE
<222> LOCATION: (51)..(51)
<223> OTHER INFORMATION: X is Y or K
<220> FEATURE:
<221> NAME/KEY: MISC_FEATURE
<222> LOCATION: (53)..(53)
<223> OTHER INFORMATION: X is V, A or M
<220> FEATURE:
<221> NAME/KEY: MISC_FEATURE
<222> LOCATION: (56)..(56)
<223> OTHER INFORMATION: X is L, A or M
<220> FEATURE:
<221> NAME/KEY: MISC_FEATURE
<222> LOCATION: (58)..(58)
<223> OTHER INFORMATION: X is K or R
<220> FEATURE:
<221> NAME/KEY: MISC_FEATURE
<222> LOCATION: (60)..(60)
<223> OTHER INFORMATION: X is V, M or I
<220> FEATURE:
<221> NAME/KEY: MISC_FEATURE
<222> LOCATION: (63)..(63)
<223> OTHER INFORMATION: X is F, R, I or Y
<220> FEATURE:
<221> NAME/KEY: MISC_FEATURE
```

```
<222> LOCATION: (64)..(64)
<223> OTHER INFORMATION: X is L, E, or A
<220> FEATURE:
<221> NAME/KEY: MISC_FEATURE
<222> LOCATION: (67)..(67)
<223> OTHER INFORMATION: X is A or L
<220> FEATURE:
<221> NAME/KEY: MISC_FEATURE
<222> LOCATION: (74)..(74)
<223> OTHER INFORMATION: X is M or L
<220> FEATURE:
<221> NAME/KEY: MISC_FEATURE
<222> LOCATION: (80)..(80)
<223> OTHER INFORMATION: X is D or Q
<220> FEATURE:
<221> NAME/KEY: MISC_FEATURE
<222> LOCATION: (84)..(84)
<223> OTHER INFORMATION: X is I, M or A
<220> FEATURE:
<221> NAME/KEY: MISC_FEATURE
<222> LOCATION: (88)..(88)
<223> OTHER INFORMATION: X is L, V or I
<220> FEATURE:
<221> NAME/KEY: MISC_FEATURE
<222> LOCATION: (89)..(89)
<223> OTHER INFORMATION: X is K, L or I
<220> FEATURE:
<221> NAME/KEY: MISC_FEATURE
<222> LOCATION: (91)..(91)
<223> OTHER INFORMATION: X is F, Y, E or L
<220> FEATURE:
<221> NAME/KEY: MISC_FEATURE
<222> LOCATION: (92)..(92)
<223> OTHER INFORMATION: X is D, A, V or M
<220> FEATURE:
<221> NAME/KEY: MISC_FEATURE
<222> LOCATION: (94)..(94)
<223> OTHER INFORMATION: X is E, I or R
<220> FEATURE:
<221> NAME/KEY: MISC_FEATURE
<222> LOCATION: (95)..(95)
<223> OTHER INFORMATION: X is V, A or L
<220> FEATURE:
<221> NAME/KEY: MISC_FEATURE
<222> LOCATION: (96)..(96)
<223> OTHER INFORMATION: X is E, F or W
<220> FEATURE:
<221> NAME/KEY: MISC_FEATURE
<222> LOCATION: (99)..(99)
<223> OTHER INFORMATION: X is L or I
<220> FEATURE:
<221> NAME/KEY: MISC_FEATURE
<222> LOCATION: (102)..(102)
<223> OTHER INFORMATION: X is M, L or I
<220> FEATURE:
<221> NAME/KEY: MISC_FEATURE
<222> LOCATION: (103)..(103)
<223> OTHER INFORMATION: X is K, M, A or L
<220> FEATURE:
<221> NAME/KEY: MISC_FEATURE
<222> LOCATION: (106)..(106)
<223> OTHER INFORMATION: X is A, V or I
<220> FEATURE:
<221> NAME/KEY: MISC_FEATURE
<222> LOCATION: (108)..(108)
<223> OTHER INFORMATION: X is R, D, I or A
<220> FEATURE:
<221> NAME/KEY: MISC_FEATURE
<222> LOCATION: (109)..(109)
<223> OTHER INFORMATION: X is M, K, L or W
<220> FEATURE:
<221> NAME/KEY: MISC_FEATURE
<222> LOCATION: (110)..(110)
<223> OTHER INFORMATION: X is A, F or V
<220> FEATURE:
<221> NAME/KEY: MISC_FEATURE
<222> LOCATION: (113)..(113)
<223> OTHER INFORMATION: X is G or optionally absent
<220> FEATURE:
```

```
<221> NAME/KEY: MISC_FEATURE
<222> LOCATION: (114)..(114)
<223> OTHER INFORMATION: X is S or optionally absent
<220> FEATURE:
<221> NAME/KEY: MISC_FEATURE
<222> LOCATION: (115)..(115)
<223> OTHER INFORMATION: X is W or optionally absent

<400> SEQUENCE: 3

Xaa Xaa Xaa Ser Asp Xaa Arg Lys Asp Xaa Glu Xaa Arg Xaa Asp Lys
1               5                   10                  15

Xaa Xaa Glu Ala Xaa Lys Asn Lys Xaa Asp Lys Xaa Lys Ala Ala Xaa
            20                  25                  30

Arg Lys Xaa Xaa Xaa Xaa Glu Glu Arg Xaa Lys Asp Xaa Xaa Lys Xaa
            35                  40                  45

Xaa Arg Xaa Glu Xaa Glu Gln Xaa Arg Xaa Ala Xaa Arg Asn Xaa Xaa
        50                  55                  60

Ser Glu Xaa Leu Ser Lys Ile Asn Asp Xaa Pro Ile Thr Asn Asp Xaa
65              70                  75                  80

Lys Lys Leu Xaa Ser Asn Asp Xaa Xaa Lys Xaa Xaa Ala Xaa Xaa Xaa
            85                  90                  95

Lys Lys Xaa Glu Ala Xaa Xaa Ala Asp Xaa Glu Xaa Xaa Xaa Thr Gln
            100                 105                 110

Xaa Xaa Xaa
        115

<210> SEQ ID NO 4
<211> LENGTH: 115
<212> TYPE: PRT
<213> ORGANISM: Artificial Sequence
<220> FEATURE:
<223> OTHER INFORMATION: Synthetic

<400> SEQUENCE: 4

Gly Ser Arg Ser Asp Met Arg Lys Asp Ala Glu Arg Arg Phe Asp Lys
1               5                   10                  15

Phe Val Glu Ala Ala Lys Asn Lys Phe Asp Lys Phe Lys Ala Ala Leu
            20                  25                  30

Arg Lys Gly Asp Ile Lys Glu Glu Arg Arg Lys Asp Met Lys Lys Leu
            35                  40                  45

Ala Arg Lys Glu Ala Glu Gln Ala Arg Arg Ala Val Arg Asn Arg Leu
        50                  55                  60

Ser Glu Leu Leu Ser Lys Ile Asn Asp Met Pro Ile Thr Asn Asp Gln
65              70                  75                  80

Lys Lys Leu Met Ser Asn Asp Val Leu Lys Phe Ala Ala Glu Ala Glu
            85                  90                  95

Lys Lys Ile Glu Ala Leu Ala Ala Asp Ala Glu Asp Lys Phe Thr Gln
            100                 105                 110

Gly Ser Trp
        115

<210> SEQ ID NO 5
<211> LENGTH: 115
<212> TYPE: PRT
<213> ORGANISM: Artificial Sequence
<220> FEATURE:
<223> OTHER INFORMATION: Synthetic

<400> SEQUENCE: 5

Gly Ser Leu Ser Asp Val Arg Lys Asp Val Glu Lys Arg Ile Asp Lys
```

-continued

```
              1               5                  10                 15
           Ala Leu Glu Ala Phe Lys Asn Lys Met Asp Lys Glu Lys Ala Phe
                          20                  25                 30

Arg Lys Asp Pro Pro Ser Glu Glu Arg Arg Lys Asp Lys Lys Lys Glu
                          35                  40                 45

Phe Arg Glu Glu Arg Glu Gln Val Arg Lys Ala Ile Arg Asn Val Leu
                          50                  55                 60

Ser Glu Ala Leu Ser Lys Ile Asn Asp Leu Pro Ile Thr Asn Asp Lys
           65                 70                  75                 80

Lys Lys Leu Val Ser Asn Asp Val Ile Lys Val Ala Glu Met Lys
                          85                  90                 95

Lys Lys Val Glu Leu Glu Val Ala Asp Val Glu Lys Lys Val Thr Gln
                          100                 105                110

Gly Ser Trp
                          115
```

<210> SEQ ID NO 6
<211> LENGTH: 112
<212> TYPE: PRT
<213> ORGANISM: Artificial Sequence
<220> FEATURE:
<223> OTHER INFORMATION: Synthetic

<400> SEQUENCE: 6

```
           Gly Ser Met Ser Asp Ala Arg Lys Asp Leu Glu Glu Arg Leu Asp Lys
           1               5                  10                 15

Leu Leu Glu Ala Ala Lys Asn Lys Met Asp Lys Phe Lys Ala Ala Met
                          20                  25                 30

Arg Lys Arg Gly Gln Arg Glu Glu Arg Lys Lys Asp Trp Ala Lys Ile
                          35                  40                 45

Val Arg Asp Glu Phe Glu Gln Phe Arg Lys Ala Val Arg Asn Phe Leu
                          50                  55                 60

Ser Glu Ala Leu Ser Lys Ile Asn Asp Tyr Pro Ile Thr Asn Asp Asp
           65                 70                  75                 80

Lys Lys Leu Thr Ser Asn Asp Thr Lys Lys Phe Ala Ala Glu Val Glu
                          85                  90                 95

Lys Lys Leu Glu Ala Phe Lys Ala Asp Val Glu Glu Ala Ala Thr Gln
                          100                 105                110
```

<210> SEQ ID NO 7
<211> LENGTH: 112
<212> TYPE: PRT
<213> ORGANISM: Artificial Sequence
<220> FEATURE:
<223> OTHER INFORMATION: Synthetic

<400> SEQUENCE: 7

```
           Gly Ser Met Ser Asp Ile Arg Lys Asp Leu Glu Glu Arg Phe Asp Lys
           1               5                  10                 15

Leu Val Glu Ala Leu Lys Asn Lys Val Asp Lys Met Lys Ala Ala Phe
                          20                  25                 30

Arg Lys Asp Gln Phe His Glu Glu Arg Met Lys Asp Trp Phe Lys Asp
                          35                  40                 45

Leu Arg Lys Glu Val Glu Gln Met Arg Arg Ala Val Arg Asn Tyr Ala
                          50                  55                 60

Ser Glu Ala Leu Ser Lys Ile Asn Asp Leu Pro Ile Thr Asn Asp Asp
           65                 70                  75                 80
```

```
Lys Lys Leu Ala Ser Asn Asp Val Leu Lys Leu Val Ala Glu Val Trp
                85                  90                  95

Lys Lys Leu Glu Ala Ile Leu Ala Asp Val Glu Ala Trp Phe Thr Gln
                100                 105                 110
```

<210> SEQ ID NO 8
<211> LENGTH: 112
<212> TYPE: PRT
<213> ORGANISM: Artificial Sequence
<220> FEATURE:
<223> OTHER INFORMATION: Synthetic

<400> SEQUENCE: 8

```
Gly Ser Phe Ser Asp Ile Arg Lys Asp Ala Glu Asp Arg Ala Asp Lys
1               5                   10                  15

Ala Phe Glu Ala Ala Lys Asn Lys Phe Asp Lys Ile Lys Ala Ala Ile
                20                  25                  30

Arg Lys Asp Trp Pro Ser Glu Glu Arg Ala Lys Asp Leu Met Lys Lys
                35                  40                  45

Ala Arg Tyr Glu Met Glu Gln Ala Arg Arg Ala Ile Arg Asn Ile Glu
                50                  55                  60

Ser Glu Ala Leu Ser Lys Ile Asn Asp Leu Pro Ile Thr Asn Asp Gln
65                  70                  75                  80

Lys Lys Leu Ala Ser Asn Asp Ile Ile Lys Glu Met Ala Arg Leu Phe
                85                  90                  95

Lys Lys Leu Glu Ala Leu Met Ala Asp Ile Glu Ile Leu Val Thr Gln
                100                 105                 110
```

<210> SEQ ID NO 9
<211> LENGTH: 115
<212> TYPE: PRT
<213> ORGANISM: Artificial Sequence
<220> FEATURE:
<223> OTHER INFORMATION: Synthetic

<400> SEQUENCE: 9

```
Gly Ser Leu Ser Asp Ile Arg Lys Asp Ala Glu Arg Arg Phe Asp Lys
1               5                   10                  15

Leu Val Glu Ala Val Lys Asn Lys Leu Asp Lys Met Lys Ala Ala Leu
                20                  25                  30

Arg Lys Glu Gly Gln Gln Glu Arg Met Lys Asp Leu Met Lys Phe
                35                  40                  45

Met Arg Lys Glu Val Gly Gln Leu Arg Lys Ala Met Arg Asn Phe Leu
                50                  55                  60

Ser Glu Ala Leu Ser Lys Ile Asn Asp Met Pro Ile Thr Asn Asp Asp
65                  70                  75                  80

Lys Lys Leu Ile Ser Asn Asp Leu Lys Lys Tyr Asp Ala Ile Ala Glu
                85                  90                  95

Lys Lys Leu Glu Ala Met Lys Ala Asp Val Glu Arg Met Ala Thr Gln
                100                 105                 110

Gly Ser Trp
        115
```

<210> SEQ ID NO 10
<211> LENGTH: 112
<212> TYPE: PRT
<213> ORGANISM: Artificial Sequence
<220> FEATURE:
<223> OTHER INFORMATION: Synthetic

<400> SEQUENCE: 10

Gly Ser Met Ser Asp Arg Arg Lys Asp Leu Glu Glu Arg Leu Asp Lys
1               5                   10                  15

Leu Leu Glu Ala Ala Lys Asn Lys Glu Asp Lys Phe Lys Ala Ala Met
                20                  25                  30

Arg Lys Arg Gly Gln Arg Glu Arg Met Lys Asp Trp Ala Lys Ile
            35                  40                  45

Ala Arg Asp Glu Phe Glu Gln Phe Arg Lys Ala Val Arg Asn Phe Leu
        50                  55                  60

Ser Glu Ala Leu Ser Lys Ile Asn Asp Tyr Pro Ile Thr Asn Asp Asp
65                  70                  75                  80

Lys Lys Leu Thr Ser Asn Asp Ala Lys Lys Phe Asp Ala Glu Val Ala
                85                  90                  95

Lys Lys Leu Glu Ala Phe Lys Ala Asp Ala Glu Ala Ala Thr Gln
                100                 105                 110

<210> SEQ ID NO 11
<211> LENGTH: 116
<212> TYPE: PRT
<213> ORGANISM: Artificial Sequence
<220> FEATURE:
<223> OTHER INFORMATION: Synthetic

<400> SEQUENCE: 11

Gly Ser Ile Ser Asp Ile Arg Lys Asp Ala Glu Val Arg Met Asp Lys
1               5                   10                  15

Ala Val Glu Ala Phe Lys Asn Lys Leu Asp Lys Phe Lys Ala Ala Val
                20                  25                  30

Arg Lys Val Phe Pro Thr Glu Glu Arg Ile Lys Asp Trp Leu Lys Ile
            35                  40                  45

Val Arg Gly Glu Ala Glu Gln Ala Arg Val Ala Val Arg Asn Val Gly
        50                  55                  60

Arg Asp Ala Asn Asp Lys Ala Ala Ala Leu Gly Lys Ala Lys Glu Ile
65                  70                  75                  80

Asn Trp Phe Asp Ile Ser Gln Ser Leu Trp Asp Val Gln Lys Leu Thr
                85                  90                  95

Asp Ala Ala Ile Lys Lys Ile Glu Ala Ala Leu Ala Asp Met Glu Ala
                100                 105                 110

Trp Leu Thr Gln
        115

<210> SEQ ID NO 12
<211> LENGTH: 112
<212> TYPE: PRT
<213> ORGANISM: Artificial Sequence
<220> FEATURE:
<223> OTHER INFORMATION: Synthetic

<400> SEQUENCE: 12

Gly Ser Leu Ser Asp Leu Met Lys Asp Leu Glu Lys Arg Phe Asp Lys
1               5                   10                  15

Phe Met Glu Ala Ile Lys Asn Lys Trp Asp Lys Val Lys Ala Ala Phe
                20                  25                  30

Arg Lys Gln Glu Lys Gly Glu Glu Arg Ala Lys Asp Met Phe Lys Ile
            35                  40                  45

Phe Arg Glu Glu Leu Glu Gln Leu Arg Lys Ala Ile Arg Asn Ala Leu
        50                  55                  60

```
Ser Glu Ala Leu Ser Lys Ile Asn Asp Leu Pro Ile Thr Asn Asp Asp
65                  70                  75                  80

Lys Lys Leu Ala Ser Asn Lys Ala Lys Lys Arg Ala Ala Arg Val Met
                85                  90                  95

Lys Lys Val Glu Ala Phe Ile Ala Asp Val Glu Ala Trp Lys Thr Gln
            100                 105                 110
```